United States Patent [19]

Ray et al.

[11] Patent Number: 4,961,740
[45] Date of Patent: Oct. 9, 1990

[54] V-THREAD FUSION CAGE AND METHOD OF FUSING A BONE JOINT

[75] Inventors: Charles D. Ray, Deephaven; Eugene A. Dickhudt, New Brighton, both of Minn.

[73] Assignee: Surgical Dynamics, Inc., Alameda, Calif.

[21] Appl. No.: 259,031

[22] Filed: Oct. 17, 1988

[51] Int. Cl.⁵ .............................. A61F 5/04; A61F 2/28
[52] U.S. Cl. ........................................ 606/61; 606/86; 623/16
[58] Field of Search ............ 128/92 YJ, 92 C, 92 CA, 128/92 UP, 92 YP, 92 YZ; 623/16, 17, 18

[56] References Cited

U.S. PATENT DOCUMENTS

| | | | |
|---|---|---|---|
| Re. 31,865 | 4/1985 | Roux | 623/18 |
| 2,537,070 | 1/1951 | Longfellow | 128/92 YJ |
| 3,720,959 | 3/1973 | Hahn | 623/16 |
| 3,783,860 | 1/1974 | Burstein et al. | 128/92 YZ |
| 4,059,115 | 11/1977 | Jumashev et al. | 128/92 YJ |
| 4,492,226 | 1/1985 | Belykh et al. | 128/92 YZ |
| 4,501,269 | 2/1985 | Bagby | 128/92 YJ |
| 4,522,200 | 6/1985 | Stednitz | 128/92 YZ |
| 4,599,086 | 7/1986 | Doty | 128/92 R |
| 4,657,550 | 4/1987 | Daher | 128/92 YM |
| 4,677,972 | 7/1987 | Tornier | 128/92 VP |

FOREIGN PATENT DOCUMENTS 2295729 12/1974 France.

*Primary Examiner*—Robert A. Hafer
*Assistant Examiner*—Kerry Owens
*Attorney, Agent, or Firm*—Fliesler, Dubb, Meyer & Lovejoy

[57] ABSTRACT

A fusion cage 10 includes a cage body defining an internal cavity with an inner surface and an outer surface. The outer surface defines a helical thread 12 comprised of a plurality of turns which define valleys 14 therebetween. Located in the valleys 14 are perforations 13 which provide communication between the outer surface and the interior cavity. Thus, when the fusion cage 10 is mated to a bone structure and the internnal cavity is packed with bone chips or other bone-growth-inducing substances, there is immediate contact between the bone structure and the bone chips through the perforations 13.

34 Claims, 1 Drawing Sheet

V-THREAD FUSION CAGE AND METHOD OF FUSING A BONE JOINT

BACKGROUND OF THE INVENTION

1. Field of the Invention

The invention concerns method and apparatus for fusing two adjacent bony structures such as a bone joint, especially adjacent vertebrae of the spine.

2. Description of Related Art

Subsequent to injury, disease or other degenerative disorder, the disc, a ligamentous cushion between vertebrae, may undergo a painful deterioration. The disc shrinks and flattens out, and the distance between the vertebral bodies begins to collapse. Subsequently, there may be a progressive degeneration leading to mechanical instability, where painful translocations occur between adjacent vertebrae. The movement-induced pain may be so disabling that in many such cases, the segmental motion must be eliminated. Thus, rigid fusions may be the only present means to stop the translocations and relieve the pain.

It is generally held that successful fusions demand a contiguous growth of bone to create a solid mass that will unite the movable elements into one unit. Otherwise, the fusion cannot achieve the tasks of pain reduction, maintenance of intervertebral height, and immobility of the segment. When fusion bone is first placed, it is soft and movable, having no cohesive strength. Therefore a variety of appliances have been developed that attempt to hold the segments quite still under conditions of normal spinal activity and daily stress. Bone graft material is placed between the segments, the outer or cortical surfaces of which have been removed or deeply scarified so as to promote the ingrowth of the graft into these recipient sites. Thus positioned, the bone graft slowly unites the segments. Such an appliance is not meant to permanently secure immobility of the segments. Bone ingrowth is required for this.

Dependency upon such an appliance as the sole stabilizer is ultimately unsuccessful due to the development of a mechanical gap or transition between the bone and the appliance, leading to structural failure of the bone and adjacent connective tissue. Such failure is seen in fractures, erosion and absorption of bone with potential further collapse. The pain may also become progressively disabling.

Approximately 150,000 lumbar spinal fusions were performed in the USA during 1987, as reported by the American Hospital Association. There are many methods for intervertebral fusion. The most successful have achieved a success rate of about 90% in random cases. However, several of these techniques, especially those requiring complex appliances, are difficult to master and are hazardous to nerve and vessel structures normally lying close to the involved bones.

From a biomechanical point of view, the most important location of a spinal fusion is at the mechanical center of rotation between the vertebrae. This point is centered within the disc space. Therefore, an interbody fusion is the most rigid and thus the most sought after method among surgeons. Current methods of interbody fusions are, however, the most hazardous of all spinal fusion methods.

Both anterior (transabdominal) and posterior surgical approaches are used for interbody fusions. Typically, a plug, dowel or segment of bone is driven tightly into a cavity carved inside the interbody, intradiscal space. Since there must be a bone-to-bone bridge created during the fusion process, connective tissue and discal tissue must be removed. Therefore, deep cuts within the bone must penetrate into the softer, cancellous region to promote bone growth across the space.

Intervertebral fusions using circular bone grafts have been reported in the orthopedic and neurosurgical literature for some years. B. R. Wiltberger in a paper published in Clinical Orthopedics, Vol 35, pp 69–79, 1964, reviewed various methods of intervertebral body fusion using posterior bone dowels driven firmly into a suitably smaller hole between the adjacent vertebrae. Upon doing so the dowel can split or crack or collapse. The stretched bone might also split and it can be compressed by the dowel to the point that it will not grow normally due to collapse of formerly open pores or vascular channels. If this occurs, there may be a late absorption of surrounding bone and the dowel might loosen, with a renewed danger of expulsion. See also a 2-page brochure from Neurological Surgery Associates of Cincinnati, Inc. entitled "Posterior Lumbar Interbody Fusion Made Simple" which shows, after the bone dowel placement, the "(a)pplication of 5 mm dacron suture around spinous processes."

U.S. Pat. No. 4,501,269 (Bagby) describes a surgical procedure for stabilizing the cervical spine of a horse and says that the procedure is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint. The process was developed to immediately stabilize the joint and to further promote ultimate bone-to-bone fusion. . . . The implanted structure is in the form of a perforated cylindrical bone basket which can be filled with bone fragments produced during the preparation of the joint. These bone fragments provide autogenous tissue to promote bone growth through the basket, as well as around it.

The process involves the initial steps of surgically accessing the joint and removing intervening cartilage located between the contiguous bony surfaces. A transverse cylindrical opening is then bored across the contiguous bony surfaces. Immediate stabilization is achieved by driving into the cylindrical opening a hollow basket having a rigid perforated cylindrical wall whose outside diameter is slightly greater than the inside diameter of the cylindrical opening. The implanting of the basket spreads the bony surfaces apart in opposition to the resistance to expansion of the joint provided by the surrounding ligaments" (col. 2, lines 26–55).

Otero-Vich, J. Neurosurg., Vol 63, pp 750–753 (1983) describes a means for cervical spine fusion, using an anterior approach, by surgically implanting a cylindrical bone graft.

"Screw threads are placed in the graft with a small, previously sterilized die. The grooves of the thread can be made as deep as required. The vertebral cervical bodies are prepared according to Cloward's technique. After a cylindrical bed has been drilled in the appropriate intervertebral bodies, the graft is screwed into place with instruments especially developed for this purpose" (p. 750).

Otero-Vich's FIG. 2 legend points out that a threaded graft dowel has a larger contact surface than a plain dowel and a greater resistance to pressure and sliding. Otero-Vich also says:

"When grafts with a diameter of 14 mm were used, we sometimes threaded the receiving bed with a diestock of 13 mm to facilitate the insertion" (p. 751).

An additional desirable effect of an intervertebral fusion is the restoration or maintenance of a normal intervertebral spacing. Spreading devices are generally required in order to restore all or a part of the normal intradiscal height, in the process of placing the fusion material or appliance. When the procedure is performed using the commonly employed posterior approach, a variety of spreaders may be placed between various posterior bony elements normally attached to the vertebrae, such as, dorsal spinous processes or laminas. Using such spreaders, a forward tilt or wedging of the discal space occurs, with the posterior aspect of the space becoming more open than the anterior. When a bone graft of any shape is driven into a cavity that is wedged more open posteriorly between two opposing movable vertebrae, there is a strong propensity for the graft to be retropulsed during the postoperative recovery period as a result of to and fro movement between the opposing vertebrae. Thus, to aid in the prevention of graft expulsion, it would be desirable to have the cavity either maintain parallelism or be slightly narrower at its most posterior portion. Ventral to this cavity, the stout ligamentous disc anulus remains and prevents ventral migration of the graft into the retroperitoneal space. Further, there is value in restoring the original spinal lordotic curve, as the fusion grows; this requires that the cavity and the interbody fusion element be placed to promote a normal spinal anatomical position, that is, without wedging of the space in either direction.

SUMMARY OF THE INVENTION

The invention provides for a fusion cage which has a threaded outer surface and an internal cavity which is adapted to be filled with bone chips. Perforations are provided in valleys between adjacent turns of the thread, which perforations provide communication between the outer surface and the internal cavity. The cage can be screwed into a threaded bore provided in the bone structure at the surgical site and then packed with the bone chips. Once done, there is immediate contact between the bone structure and the bone chips in order to promote fusion.

Mating of the threads ensures that the fusion basket remains securely in place, there being much less danger of splitting or compression atrophy of the recipient bone. Eventually, the ingrowth of bone through perforations in the valley of the thread forms a permanent interconnection between the two bony structures.

By V-thread is meant that the crown of the thread is sharp, although its valley preferably is blunt or rounded to permit the mating peaks of the female threads to have adequate strength. When the angle of the V-thread at its crown is about 60°, a preferred range of radii for the fillet in the valley is from 0.35 to 0.75 mm. The angle at the crown of the V-thread should be no more than 90°, because a sharper thread would increase the exposed interface surface of bone relative to the implant, thus increasing the opportunity for ingrowth. However, the angle at the crown should be at least 45°, because the pitch would be undesirably small if the angle were smaller. An unduly small pitch would entail weak female bone threads and create a danger of cross threading.

The perforations should be as large as possible as long as the fusion basket has adequate structural strength. When the surface of the fusion basket is projected onto the inner face of a cylinder, the projected perforations should comprise from 30% to 60% of the projected area, preferably about 50%. Individual apertures should be at least one mm both axially and transversely to permit good ingrowth of fresh bone, whereas the fusion basket might be unduly weakened if the apertures were substantially more than 2 mm axially and 3 mm transversely when the angle of the V-thread at its crown is about 60°.

The novel fusion basket preferably is fitted with end caps, a first of which may be in place before the fusion basket is screwed into the recipient bone, and thus should have a maximum diameter no greater than the minor diameter of the V-thread of the fusion basket. The first end cap retains the bone-inducing substance when it is packed into the fusion basket. The open end of the fusion basket may then be closed with a second end cap to hold the bone chips securely in place. The end caps may be imperforate but preferably have substantially the same perforation as does the fusion basket to permit bone or other tissue ingrowth through the end caps. However, end caps may not be necessary or, if used, they can be made of biodegradable material, even when the fusion basket is not.

Currently the novel V-thread fusion basket preferably is made of implantable-grade stainless steel. Titanium and ceramics are also useful, as are super-strength polymers or composites of polymers and high-strength filaments such as super-high-density polyethylene, glass, or graphite. Non-metallic composites have the preferred ability to pass x-rays or magnetic beams without distortion, thus enhancing the preparation of scan images as compared to metallic fusion baskets. The fusion basket can be biodegradable, because it no longer is needed after the bone ingrowth has matured. When the fusion basket is not biodegradable, it can remain in place permanently after the ingrowth has taken place, in contrast to the need to remove many types of metallic supports or appliances that have heretofore been used to promote rigid fusions.

Useful bone-inducing substances include bone chips and bone substitutes or synthetic material, with or without bone activating matter, such as hydroxyapatite, bone morphologic protein, bone growth factor, or cartilage activation factor. Instead of being mixed with the bone-inducing substance, bone activating matter can be coated onto the novel fusion basket, e.g., after being microencapsulated in a wax. When the fusion basket is made of an organic material, bone activating matter can be combined with the organic material before it is formed into the fusion basket.

For implantation between vertebrae of a person's lower back, two sizes of the novel fusion basket should suffice, one having a V-thread major diameter of 16 mm and the other a major diameter of 12 mm. Because the anterior-posterior dimension of a typical lower lumbar vertebra is about 30 mm, the length of the fusion basket preferably does not exceed 25 mm but is at least 20 mm in length to give sufficient contact as well as a good platform when implanted in pairs.

The crown of the V-thread of the novel fusion basket preferably is continuous, both for strength and for ease of insertion into the threaded bore. Preferably the V- thread has from 3 to 8 turns per cm. A smaller turn ratio may result in an undesirably large thread depth, penetrating too deeply into the cancellous bone. A larger turn ratio may unduly restrict the size of the perforations.

The novel V-thread fusion basket can be implanted for fusing adjacent bony structures by the following method:

(a) forming in said bony structures a bore with a female thread that penetrates into their cancellous regions, (b) forming a rigid, perforate, cylindrical basket to have an external, substantially continuous helical V-thread that can mate with said female thread, (c) screwing the basket into said threaded bore, and (d) packing the basket with bone-inducing substance.

When the bore to be formed in step (a) is to extend between adjacent vertebrae, there should be prior to step (a) the added step of spreading the vertebrae apart, preferably in a manner that maintains their parallelism, the fusion basket is implanted in pairs on opposite sides of the disc space.

The novel fusion basket should have a modulus of elasticity approximating that of the recipient bone, thus permitting it to flex along its length, consequently minimizing stresses at the bony interface between the graft and recipient bone. Although a fusion basket of substantially lower modulus of elasticity would provide the same desirable result, it might not have adequate structural strength.

The bore into which the V-thread fusion basket is to be inserted preferably is tapped by hand, using a slow motion to ensure against burning the bone. This freshens the bone margins of the bore so that if any bone had been burned by drilling to form the bore, it is now cut away slowly by hand. The tapping process is quite safe, in that the surgeon can feel the progress of the technique.

The V-thread fusion basket preferably is screwed by hand into the threaded bore, again permitting the surgeon to feel if the resistance is too great and that rethreading of the bore might be required. In contrast, a bone dowel typically is driven into a bore using a hammer, and in order to guard against an overly tight fit, the surgeon listens to the sound of the striking hammer and also monitors the degree of resistance.

When using the novel fusion basket to create bone ingrowth between adjacent vertebrae, the fusion basket should be implanted in pairs on opposite sides of the disc space. Each is held in place by its V-thread, biting into female threads that penetrate into the cancellous bone of the interposed vertebral bodies. Gravity, muscle pull and elastic recoil of the spread (or stretched) outer disc anulus together exert force against each of the fusion baskets. Thus the fusion baskets are held in place by compression forces between the adjacent vertebrae.

To prevent distraction forces from possibly dislodging the fusion baskets, e.g., when the patient forward flexes, thus separating the posterior margins of the adjacent vertebrae, the dorsal processes may be tied or wrapped together. By another technique, screws placed through the appropriate facet jackets limit both flexion and extension motions.

A novel interbody spreader in the form of a scissors jack has been developed to maintain a desirable parallel attitude between the adjacent vertebrae while the bore is drilled and then tapped by a novel instrument. Another instrument that has been developed for use in the implantation of the novel fusion basket is a tapping instrument for forming helical threads in a bore in recipient bone. This novel tapping instrument comprises a hollow cylindrical shaft having a handle at one end and an external thread which is formed at the other end with at least one scallop that exposes a cutting edge, and a pilot rod that slidably fits into said bore, projects beyond said other end of the hollow shaft, and is formed with a central recess that communicates with the scallop in the hollow shaft and provides a reservoir for detritus removed by said cutting edge, thus permitting the detritus to be carried away by removing the pilot rod from the hollow shaft. The portion of the pilot rod that projects beyond said other end of the hollow shaft preferably is threaded to carry detritus upwardly to the reservoir.

When using the novel tapping instrument to form female threads for an interbody fusion, the hollow shaft should have an odd number of scallops and cutting edges, preferably three, because an odd number provides more equal removal of recipient bone on both sides of the bore than would an even number.

The novel tapping instrument and a novel wrench are illustrated in the drawing that also illustrates two V-thread fusion baskets of the invention.

THE DRAWING

In the drawing, all figures of which are schematic,

Figure 1:
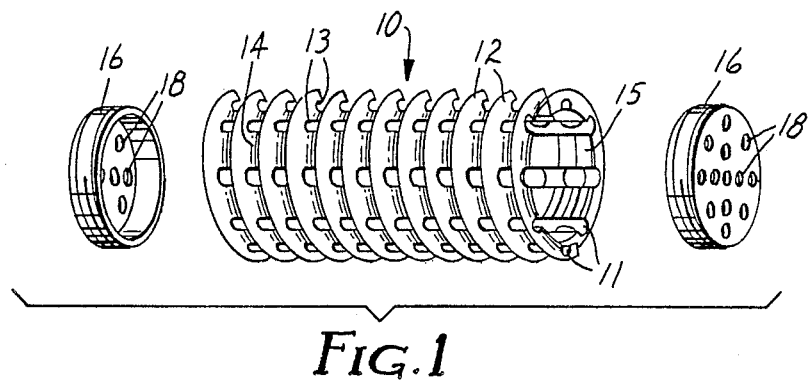
FIG. 1 is an exploded isometric view of a first V-thread fusion basket of the invention and two perforated end caps.

The fusion basket 10 of FIG. 1 was formed from a solid steel cylinder by drilling eight small, equally spaced holes 11 in the axial direction, each hole being centered on a circle concentric with the axis of the cylinder. Then a large hole was drilled centered on the axis and having a radius substantially identical to that of the aforementioned circle. A V-thread 12 was then machined in the external surface of the cylinder, thus opening through that surface a perforation 13 extending through the rounded valley 14 of the V-thread at each crossing of the valley and one of the small holes 11. A screw thread 15 was then machined in the internal surface of the fusion basket to threadably receive an end cap 16 that has apertures 18 similar to those of a salt shaker. Snap-on end caps would also be useful.

In making a fusion basket by the technique described in the preceding paragraph, the small holes 11 could be enlarged to intersect each other, thus making it unnecessary to drill a central hole. Enlarged small holes would result in larger perforations 13.

Figure 2:
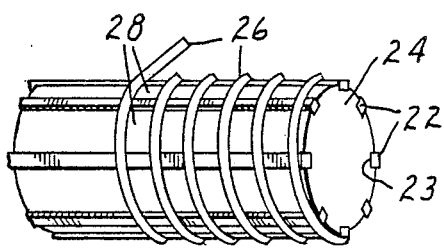
FIG. 2 is an isometric view illustrating the formation of a body that can be cut to form a series of second V-thread fusion baskets of the invention.

Referring to FIG. 2, a series of fusion baskets can be made from a plurality of rods 22 of rectangular cross-section that can be continuously extruded and fed into each of eight keyways 23 in the surface of a mandrel 24. Simultaneously, a rod 26 of triangular cross-section is extruded, wrapped helically around the rectangular rods 22, and soldered or welded to each of the rectangular rods 22 at every crossing to provide an external V-thread. Upon emerging from the keyways, the resulting body is cut into individual fusion baskets each of which has a perforation 28 between adjacent turns of the V-thread-forming rod 26 wherever it bridges a gap between adjacent rectangular rods 22.

A fusion basket identical to that of FIG. 2 can be made from a hollow cylinder by machining an external V-thread and broaching a plurality of rectangular internal keyways.

Each of the fusion baskets of FIGS. 1 and 2 could be made from a model by the lost wax process.

Figure 3:
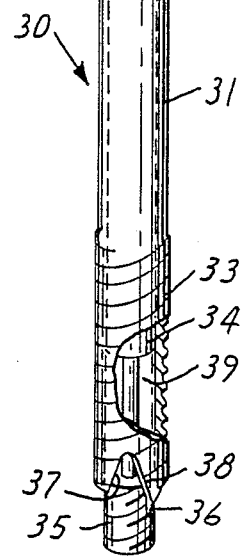
FIG. 3 is an isometric view of a tap (partly cut away to reveal details of construction) for forming female threads in bores into which a V-thread fusion basket is to be inserted.
Figure 1:
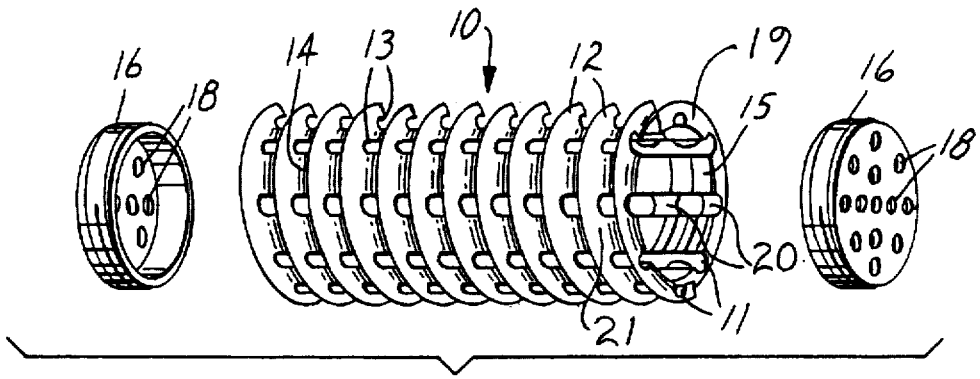
Figure 2:
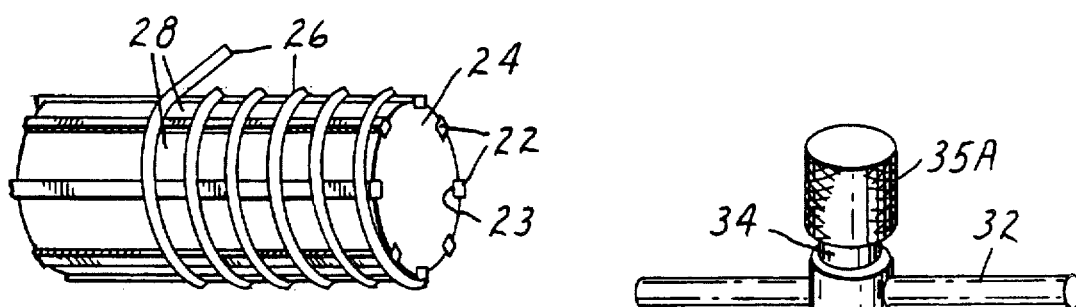
Figure 4:
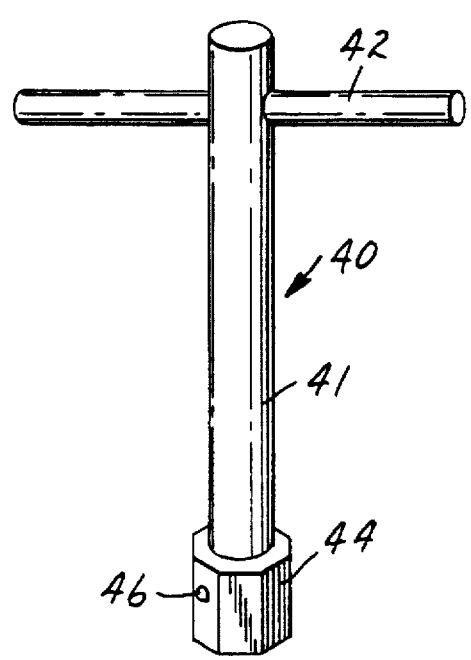
Figure 3:
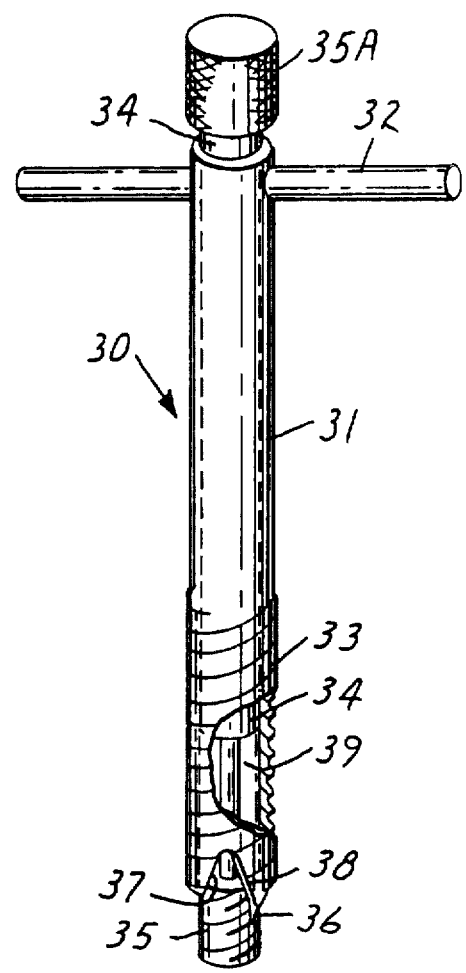

The tapping instrument 30 of FIG. 3 has a hollow cylindrical shaft 31 with a T-handle 32 at one end and an external thread 33 at the other end. Slidably received within the hollow shaft is a pilot rod 34, one end 35 of which protrudes beyond the hollow shaft 31 and slidably fits into a bore that has been drilled into the recipient bone. At the other end of the pilot rod is a knurled cap 35A. Projecting from the threaded end of the hollow shaft 31 are cutting teeth 36 that enlarge the bore to the minor diameter of the external thread 33 of the hollow shaft 31. The threaded end of the hollow shaft also is formed with three symmetrical scallops 37 (one shown) to expose a cutting edge 38 at the leading edge of the external thread 33, which cutting edge forms female bone threads in the bore upon rotation of the hollow shaft.

Detritus created by tapping instrument 30 is deposited through the scallops 37 into a reservoir provided by a central recess 39 in the pilot rod 34. The end 35 of the pilot rod which extends from the recess 39 into the bore has external threads which, when the threaded pilot rod 34 is turned, carry detritus upwardly to be deposited through the scallops into the reservoir.

Upon rotating the hollow shaft 31 to form female bone threads in the bore, the surgeon can feel increased back pressure when the reservoir becomes full and should grasp the knurled cap 35A to remove and clean out the pilot rod. If the gummy nature of the detritus were to prevent the pilot rod from being easily pulled out of the hollow shaft, the knurled cap 35A could be removed to permit the hollow shaft 31 to be unscrewed from the threaded bore, leaving the pilot rod in place. The pilot rod then serves as a guide if the bore has not yet been completely tapped and it is necessary to reinsert the hollow shaft to complete the tapping.

Figure 4:
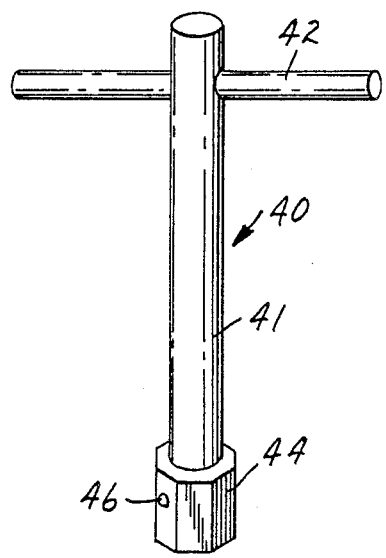
FIG. 4 is an isometric view of a wrench for screwing a V-thread fusion basket into a threaded bore.

The wrench 40 of FIG. 4 has a cylindrical shaft 41 with a T-handle 42 at one end and an octagonal protuberance 44 at the other end. The corners of the protuberance 44 fit into recesses in the fusion basket to permit the fusion basket to be rotated by rotating the wrench. A spring-loaded ball 46 frictionally holds the protuberance in place when it is inserted into the fusion basket.

IMPLANTING THE FUSION BASKET

In order to implant the novel fusion basket between adjacent vertebrae, soft, collagenous disc material is first removed from the intervertebral space. A small window is created in the overlying laminas of each side, namely, standard laminotomies. The neural tissues, dural sac and nerves, are retracted medially. The intervertebral space is cleaned of disc material in a standard surgical fashion. If the disc space has narrowed as a result of degeneration, a scissors-jack type vertebral spreader or a hydraulically inflated bladder is inserted on one (the first) side inside the disc space and opened until the space approximates the normal. This may be confirmed by a lateral x-ray. The height of the disc space is measured on the x-ray so that the proper sizes of drills, tap, and fusion basket may be chosen.

The opposite (second) side of the same disc space is then addressed. The nerve tissues on the first side are relaxed and then retracted medialward on the second side. A pilot drill (e.g., 5 mm or 8 mm diameter depending upon discal space height) cuts a small channel in the face of each of the vertebrae, penetrating the interdiscal space to a depth of about 25 mm (the normal disc space is about 30 mm deep and 50 mm wide). A drill stop may be applied to the drill to prevent overboring the hole. A solid rod pilot is then inserted into the pilot hole and a pilot cutter (7 mm or 10 mm) is passed over it and brought downward to enlarge the pilot channels to slidably receive the pilot rod 35 of the tapping instrument 30 of FIG. 3. The cutting thread 33 (12 mm or 16 mm major diameter) cuts female bone threads through the opposing vertebral end plates and into both cancellous regions that will invite the ingrowth of new bone.

A V-thread fusion basket of the invention, with one end cap in place, is snapped onto the wrench 40 of FIG. 4 by which it is screwed by hand into the threaded intradiscal bore to its full depth. After removing the wrench, the basket is packed with bone chips or other bone-inducing substance, and the second end cap is applied to hold the bone chips securely in place.

After removing the vertebral spreader, the dura and nerves on the second side are relaxed and attention is once again directed to the first side which is drilled and tapped to receive a second fusion basket by the same procedure.

Over a period of several weeks, the bone from the vertebral bodies will grow through the perforations in the fusion baskets and unite with the bone-inducing substance inside them, creating a solid fusion.

It is believed that the novel fusion baskets will primarily be implanted by a posterior approach to the spine, although an anterior approach may be utilized, especially when applied to the cervical spine.

EXAMPLE 1

The fusion basket of FIG. 1 has been machined from a cylinder of surgically implantable stainless steel to have the following dimensions:

| | |
|---|---|
| diameter of starting cylinder | 16 mm |
| length of cylinder | 25 mm |
| diameter of each small hole 11 | 3 mm |
| diameter of circle on which holes 11 are centered | 11.5 mm |
| diameter of central hole | 11 mm |
| pitch of V-thread 12 | 2.5 mm/turn |
| angle at crown of thread 12 | 60° |
| fillet radius in valley of thread 12 | 0.4 mm |
| axial width of perforations 13 | 1.6 mm |
| circumferential breadth of perfs. 13 | 2.8 mm |
| when projected onto interior of a cylinder, % of area perforated | 25% |

A V-thread fusion basket identical in appearance to one produced as in FIG. 2 can be made from a hollow cylindrical tube. After machining an external thread, a plurality of rectangular keyways are broached in the inner surface to form perforations through the valley of the thread. A continuous technique for making a novel fusion basket starts with a continuous helical spring made from a triangular rod such as the rod 26 used in FIG. 2, then welding or soldering the inner-facing surface of the spring to a plurality of cylindrical wires, each extending parallel to the axis of the spring.

What is claimed:

1. A fusion cage adapted for promoting fusion with one or more bone structures when bone-growth-inducing substance is packed into the fusion cage, comprising:
   a cage body defining an internal cavity adapted to be packed with the bone-growth-inducing substance, which cage body defining an outer surface;
   means defined on the outer surface of the cage body for mating the fusion cage to the bone structure, which means prevents the fusion cage from backing out from the bone structure;
   means for providing immediate contact between the one or more bone structures and the bone-growth-inducing substance packed into the fusion cage when the fusion cage is mated to the one or more bone structures so that the one or more bone structures cross over the outer surface into the internal cavity and into contact with the bone-growth-inducing substance packed in the fusion cage, and the bone-growth-inducing substance packed in the fusion cage.

2. The fusion cage of claim 1 wherein said internal cavity of said cage body defines an inner surface; and
   wherein said means for providing immediate contact includes a plurality of sites where the inner surface meets the outer surface.

3. The fusion cage of claim 1,
   wherein said internal cavity of said cage body defines an inner surface;
   wherein said mating means includes a thread with a plurality of turns and with valleys defined between said turns; and
   wherein said means for providing immediate contact includes a plurality of perforations defined in said valleys so that the inner surface contacts the outer surface.

4. The fusion cage of claim 1 wherein:
   said mating means including a thread with a plurality of turns, and with valleys defined between said turns; and
   said means for providing immediate contact including a plurality of channels which communicate with said internal cavity, which channels define an inner surface and which channels pierce through the valleys to define a plurality of perforations whereby the inner surface contacts the outer surface, such channels also adapted to be packed with bone-growth-inducing substance so that there is immediate contact between the one or more bone structures and the bone-growth-inducing substance.

5. The fusion cage of claim 1:
   wherein said cage body includes a plurality of spaced elongate members which define said outer surface and which elongate members have inner surfaces which define said internal cavity;
   said mating means including a helical thread member formed about and connected to the outer surface of the spaced elongate member, which helical thread member defines a plurality of adjacent turns; and
   wherein said means for providing immediate contact includes a plurality of apertures defined between adjacent turns which apertures are bordered by the spaced elongate member.

6. The fusion cage of claim 1:
   wherein said cage body includes a helical structure with an outer surface and which helical structure has an inner surface, which inner surface defines said internal cavity;
   said outer surface of the helical structure being substantially V-shaped and adapted for biting into the one or more bone structures; and
   said helical structure defining a plurality of spaced turns communicating with the internal cavity so that the inner surface contacts the outer surface such that with the outer surface biting into the bone structure, their is immediate contact between the one or more bone structures and with the bone-growth-inducing substance packed into the internal cavity of the fusion cage.

7. The fusion cage of claim 1 wherein:
   said outer surface defines an external substantially continuous V-thread adapted for mating to the bone structure;
   which thread has a multiplicity of turns and valleys defined between said turns; and
   said means for providing immediate contact includes a multiplicity of perforations located in said valleys and providing communication between said outer surface and said internal cavity.

8. A fusion cage as defined in claim 7 wherein the V-thread is continuous and the angle at the crown of the V-thread is not more than 90°, but not less than 45°.

9. A fusion cage as defined in claim 7 wherein the angle at the crown of the V-thread is about 60°.

10. A fusion cage as defined in claim 7 wherein the V-thread has from 3 to 8 turns per cm.

11. A fusion cage as defined in claim 8 wherein the valleys of the V-thread have fillets, the radius of which is from 0.35 to 0.75 mm.

12. A fusion cage as defined in claim 7 wherein, the internal cavity defines an inner surface and wherein said perforations comprise at least from 30% to 60% of said inner surface.

13. A fusion cage as defined in claim 1 which is fitted with removable perforated end caps.

14. A fusion cage as defined in claim 7, the major diameter of which is from 12 to 16 mm.

15. A fusion cage as defined in claim 1 made of implantable-grade stainless steel.

16. A fusion cage as defined in claim 1 made of X-ray-transparent material.

17. A fusion cage as defined in claim 1 wherein the cage body has a modulus of elasticity of about that of the bone structure.

18. The fusion cage as defined in claim 1:
    wherein the cage body has a width and a length, which length is greater than the width; and
    wherein the cage body has a modulus of elasticity of about that of the bone structure so that the cage body can flex with the bone structures along the length of the cage body.

19. The fusion cage as defined in claim 1 wherein the cage body is comprised of a biodegradable material.

20. The fusion cage as defined in claim 1 wherein the cage body is in part comprised of bone-activating material.

21. The fusion cage as defined in claim 1 wherein the cage body is coated with bone-activating material.

22. The fusion cage as defined in claim 1 wherein said means for providing immediate contact is substantially uniformly distributed throughout the outer surface of the cage body.

23. The fusion cage as defined in claim 7 wherein the V-thread are substantially sharp with the valleys are substantially rounded.

24. The fusion cage as defined in claim 1 wherein said internal cavity has at least one open end, and said fusion cage including an end cap and means for securing said end cap to said cage body in order to cover said open end.

25. A fusion cage of claim 1 made of magnetic signal transparent material.

26. A fusion cage of claim 1 wherein the internal cavity includes at least one opening into which is introduced the bone-growth-inducing substances, and including an end cap for covering the opening, which end cap is made of a material which is transparent to x-rays and magnetic signals.

27. A fusion cage adapted for promoting fusion with one or more bone structures when bone-growth-inducing substance is packed into the fusion cage, comprising:
a cage body having an inner surface which defines a cavity adapted to be packed with the bone-growth-inducing substance;
said cage body defining an outer surface;
means defined on the outer surface of the cage body adapted for allowing the fusion cage to bite into the bone structure;
means for providing a plurality of sites where the inner surface contacts the outer surface in order to allow immediate contact between the one or more bone structures and the bone-growth-inducing substance packed into the fusion cage.

28. A fusion cage adapted for promoting fusion of one or more bone structures when bone-growth-inducing substance is packed into the fusion cage, comprising:
a cage body defining a cavity with an inner surface, said cavity adapted to be packed with the bone-growth-inducing substance;
said cage body defining an outer surface;
means for defining threads on the outer surface of the cage body and adapted for biting into the bone structure;
said threads defining means including a plurality of threads which define valleys therebetween;
a plurality of perforations provided in the valleys of the threads for providing communication between the outer surface and the cavity in order to allow immediate contact between the one or more bone structures and the bone-growth-inducing substance packed into the fusion cage.

29. A fusion cage adapted for promoting fusion with one or more bone structures when bone-growth-inducing substance is packed into the fusion cage, comprising:
a cage body defining a cavity with an inner surface, said cavity adapted to be packed with bone-growth-inducing substance;
said cage body defining an outer surface comprised of a substantially continuous thread with a plurality of turns and valleys defined between said turns;
a plurality of perforations defined in said valleys so that the inner surface contacts the outer surface in order to allow immediate contact between the one or more bone structures and the bone-growth-inducing substance packed into the fusion cage.

30. A fusion cage adapted for promoting the fusion with one or more bone structures when bone-growth-inducing substance is packed into the fusion cage comprising:
a cage body defining a cavity with an inner surface, the cavity being adapted to be packed with bone-growth-inducing substance;
said cage body defining an outer surface comprised of a substantially continuous thread with a plurality of turns and valleys defined between adjacent turns;
said cavity defining a plurality of channels which pierce through the valleys to define a plurality of perforations whereby the inner surface contacts the outer surface so that there is immediate contact between the one or more bone structures and the bone-growth-inducing substance packed into the fusion cage.

31. A fusion cage adapted for promoting fusion with one or more bone structures when bone-growth-inducing substance is packed into the fusion cage comprising:
a plurality of spaced elongate members which define an internal cavity;
said elongate members having an inner surface that faces the internal cavity and an outer surface that faces away from the internal cavity;
a helical thread member formed about and connected to the outer surfaces of the spaced elongate members, which helical thread member defines a plurality of turns; and
a plurality of apertures defined between turns, which apertures are bordered by the spaced elongate members, wherein the thread member is adapted to contact the bone structure and provide immediate contact between the one or more bone structures and the bone-growth-inducing substance packed into the fusion cage.

32. A fusion cage adapted for promoting the fusion with one or more bone structures when bone-growth-inducing substance is packed into the fusion cage, comprising:
a helical structure having an inner surface which defines an internal cavity;
said helical structure having a substantially V-shaped outer surface pointing in a direction away from the internal cavity and adapted for biting into the one or more bone structures;
said helical structure defining a plurality of spaced turns communicating with the internal cavity so that the inner surface intersects the outer surface such that with the outer surface biting into the one or more bone structures, there is immediate contact between the one or more bone structures and the bone-growth-inducing substance packed into the internal cavity of the fusion cage.

33. A surgical method for fusing a fusion cage with one or more bone structures comprising the steps of:
forming a bore with an internal thread, in the one or more bone structures;
screwing the fusion cage into the bore which fusion cage includes:
(a) a cage body defining an internal cavity with an inner surface, and the cage body having an outer surface defining an external thread that mates with the internal thread, the external thread having a plurality of adjacent turns which define valleys therebetween; and
(b) a multiplicity of perforations located in the valleys in such a manner that the inner surface contact the outer surface;
said screwing step further causing the one or more bone structures to extend through the perforations and into the internal cavity;

packing the fusion cage with bone-growth-inducing substance in such a manner that the bone-growth-inducing substance contacts the one or more bone structures and the outer surface.

34. A fusion cage adapted for promoting the fusion with one or more bone structures when bone-growth-inducing substance is packed into the fusion cage, comprising:

a helical structure having an inner surface which defines an internal cavity;

said helical structure having an outer surface pointing in a direction away from the internal cavity and adapted for contacting one or more bone structures;

said helical structure defining a plurality of spaced turns communicating with the internal cavity such that with the outer surface contacting the one or more bone structures, there is immediate contact between the one or more bone structures and the bone-growth-inducing substance packed into the internal cavity of the fusion cage.

* * * * *

UNITED STATES PATENT AND TRADEMARK OFFICE
CERTIFICATE OF CORRECTION

PATENT NO. : 4,961,740
DATED : October 9, 1990
INVENTOR(S) : Charles D. Ray

It is certified that error appears in the above-identified patent and that said Letters Patent is hereby corrected as shown below:

Col. 9, Claim 1, the end of line 21 through line 23, please delete the words ", and the bone-growth-inducing substance packed in the fusion cage".

Col. 10, Claim 6, line 13, please delete the word "their" and insert therefor --there--.

Signed and Sealed this

Tenth Day of November, 1992

*Attest:*

DOUGLAS B. COMER

*Attesting Officer*     Acting Commissioner of Patents and Trademarks

REEXAMINATION CERTIFICATE (3104th)

United States Patent [19]

Ray et al.

[11] B1 4,961,740
[45] Certificate Issued  Jan. 14, 1997

[54] V-THREAD FUSION CAGE AND METHOD OF FUSING A BONE JOINT

[75] Inventors: Charles D. Ray, Deephaven; Eugene A. Dickhudt, New Brighton, both of Minn.

[73] Assignee: Surgical Dynamics, Incorporated, Alameda, Calif.

Reexamination Request:
No. 90/003,433, May 13, 1994

Reexamination Certificate for:
Patent No.: 4,961,740
Issued: Oct. 9, 1990
Appl. No.: 259,031
Filed: Oct. 17, 1988

Certificate of Correction issued Nov. 10, 1992.

[51] Int. Cl.$^6$ ............................... A63F 2/44; A63F 2/28
[52] U.S. Cl. ............................... 606/61; 606/86; 623/16
[58] Field of Search ............................... 606/61, 86, 16

[56] References Cited

U.S. PATENT DOCUMENTS

| Re. 31,628 | 7/1984 | Allgower et al. | 128/92 D |
|---|---|---|---|
| 3,112,743 | 12/1963 | Cochran et al. | 128/92 |
| 3,298,372 | 1/1967 | Feinberg . | |
| 3,426,364 | 2/1969 | Lumb | 3/1 |
| 3,486,505 | 12/1969 | Morrison . | |
| 3,514,791 | 6/1970 | Sparks | 3/1 |
| 3,625,198 | 12/1971 | Sparks | 128/1 |
| 3,719,186 | 3/1973 | Merig, Jr. . | |
| 3,848,601 | 11/1974 | Ma et al. | 128/305 |
| 3,849,805 | 11/1974 | Leake et al. | 3/1 |
| 3,852,045 | 12/1974 | Wheeler et al. | 29/182 |
| 3,855,638 | 12/1974 | Pilliar | 3/1 |

(List continued on next page.)

FOREIGN PATENT DOCUMENTS

| 073177A2 | 3/1983 | European Pat. Off. . |
|---|---|---|
| 0260044A1 | 3/1988 | European Pat. Off. . |
| 0260222A2 | 3/1988 | European Pat. Off. . |
| 0269175A2 | 6/1988 | European Pat. Off. . |
| 0269176A2 | 6/1988 | European Pat. Off. . |
| 2295729 | 12/1974 | France . |
| 1961531 | 7/1970 | Germany . |
| 3505567A1 | 6/1986 | Germany . |
| 56-34731 | 8/1981 | Japan . |
| 57-29348 | 2/1982 | Japan . |
| 58-78653 | 5/1983 | Japan . |
| 61-135652 | 6/1986 | Japan . |
| 62-501129 | 5/1987 | Japan . |
| 62-164458 | 7/1987 | Japan . |
| 63-43654 | 2/1988 | Japan . |
| 63-158045 | 7/1988 | Japan . |
| 1-502402 | 8/1989 | Japan . |
| 1-314560 | 12/1989 | Japan . |
| 3-503133 | 7/1991 | Japan . |
| 283078 | 2/1985 | Spain . |
| WO88/03781 | 6/1988 | WIPO . |
| WO90/00037 | 1/1990 | WIPO . |

OTHER PUBLICATIONS

Kioyshi Kaneda and Isao Yamamoto, "Spinal Instrumentation Surgery In Lumbar and Lumbosacral Spine," *The Improvement of Medicine*, vol. 147, No. 14, Dec. 31, 1988.

Hiroshi Yamamoto, "Spinal Instrumentation For Lumbar Spine—Segmental Transverse Wiring For Spondylolysis and Pedicular Screw–Spinal Plate For Spondylolisthesis," *The Improvement of Medicine*, vol. 145, No. 1, Apr. 2, 1988.

(List continued on next page.)

*Primary Examiner*—Raleigh Chiu

[57] ABSTRACT

A fusion cage 10 includes a cage body defining an internal cavity with an inner surface and an outer surface. The outer surface defines a helical thread 12 comprised of a plurality of turns which define valleys 14 therebetween. Located in the valleys 14 are perforations 13 which provide communication between the outer surface and the interior cavity. Thus, when the fusion cage 10 is mated to a bone structure and the internnal cavity is packed with bone chips or other bone-growth-inducing substances, there is immediate contact between the bone structure and the bone chips through the perforations 13.

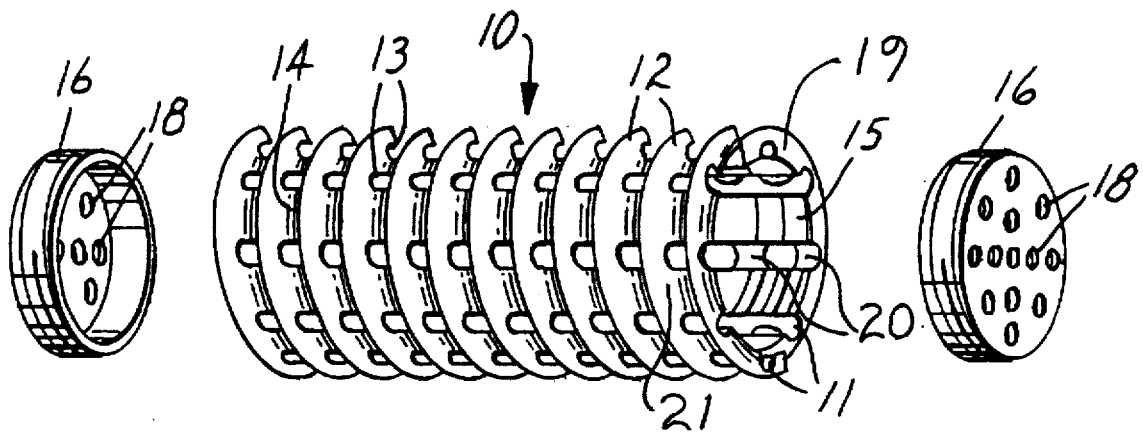

U.S. PATENT DOCUMENTS

| | | | |
|---|---|---|---|
| 3,867,728 | 2/1975 | Stubstad et al. | 3/1 |
| 3,871,031 | 3/1975 | Boutin | 3/1 |
| 3,905,047 | 9/1975 | Long | 3/1.9 |
| 3,906,550 | 9/1975 | Rostoker et al. | 3/1.912 |
| 3,916,907 | 11/1975 | Peterson | 128/345 |
| 4,124,026 | 11/1978 | Berner et al. | 128/303 R |
| 4,177,524 | 12/1979 | Grell et al. | 3/1.9 |
| 4,180,910 | 1/1980 | Straumann et al. | 433/173 |
| 4,185,383 | 1/1980 | Heimke et al. | 433/173 |
| 4,259,072 | 3/1981 | Hirabayashi et al. | 433/173 |
| 4,289,123 | 9/1981 | Dunn | 128/84 R |
| 4,309,777 | 1/1982 | Patil | 3/1.91 |
| 4,328,593 | 5/1982 | Sutter et al. | 3/1.91 |
| 4,349,921 | 9/1982 | Kuntz | 3/1 |
| 4,401,112 | 8/1983 | Rezaian | 128/92 B |
| 4,484,570 | 11/1984 | Sutter et al. | 128/92 D |
| 4,493,317 | 1/1985 | Klaue | 128/92 D |
| 4,513,744 | 4/1985 | Klaue | 128/92 D |
| 4,545,374 | 10/1985 | Jacobson . | |
| 4,549,319 | 10/1985 | Meyer | 623/22 |
| 4,553,273 | 11/1985 | Wu | 623/18 |
| 4,573,448 | 3/1986 | Kambin . | |
| 4,599,084 | 7/1986 | Nashef | 623/16 |
| 4,611,581 | 9/1986 | Steffee | 128/69 |
| 4,636,217 | 1/1987 | Ogilvie et al. | 623/17 |
| 4,653,481 | 3/1987 | Howland et al. | 128/69 |
| 4,653,486 | 3/1987 | Coker | 128/92 YF |
| 4,655,199 | 4/1987 | Steffee | 128/69 |
| 4,662,891 | 5/1987 | Noiles | 623/22 |
| 4,677,972 | 7/1987 | Tornier | 128/92 V |
| 4,714,469 | 12/1987 | Kenna | 623/17 |
| 4,721,103 | 1/1988 | Freedland | 128/92 YW |
| 4,736,738 | 4/1988 | Lipovsek et al. | 128/92 V |
| 4,743,256 | 5/1988 | Brantigan | 623/17 |
| 4,743,260 | 5/1988 | Burton | 623/17 |
| 4,769,041 | 9/1988 | Morscher | 623/22 |
| 4,772,287 | 9/1988 | Ray et al. | 623/17 |
| 4,790,297 | 12/1988 | Luque | 128/69 |
| 4,790,303 | 12/1988 | Steffee | 128/924 M |
| 4,802,468 | 2/1989 | Powlan | 128/92 V |
| 4,820,305 | 4/1989 | Harms et al. | 623/16 |
| 4,834,757 | 5/1989 | Brantigan | 623/17 |
| 4,842,517 | 6/1989 | Kawahara et al. | 433/173 |
| 4,863,474 | 9/1989 | Brown et al. | 623/16 |
| 4,877,020 | 10/1989 | Vich | 128/92 V |
| 4,878,915 | 11/1989 | Brantigan | 623/17 |
| 4,904,260 | 2/1990 | Ray | 623/17 |
| 4,936,851 | 6/1990 | Fox et al. . | |
| 5,015,247 | 5/1991 | Michelson | 606/61 |
| 5,015,255 | 5/1991 | Kuslich . | |
| 5,059,193 | 10/1991 | Kuslich . | |
| 5,062,845 | 11/1991 | Kuslich et al. . | |
| 5,147,402 | 9/1992 | Bobler et al. . | |
| 5,195,541 | 3/1993 | Obenchain . | |
| 5,263,953 | 11/1993 | Bagby . | |
| 5,313,962 | 5/1994 | Obenchain . | |
| 5,354,302 | 10/1994 | Ko . | |
| 5,357,983 | 10/1994 | Mathews . | |
| 5,423,817 | 6/1995 | Lin . | |
| 5,439,464 | 8/1995 | Shapiro . | |
| 5,445,639 | 8/1994 | Kuslich et al. . | |
| 5,458,638 | 10/1995 | Kuslich et al. . | |
| 5,484,437 | 1/1996 | Michelson . | |
| 5,489,308 | 2/1996 | Kuslich et al. . | |

OTHER PUBLICATIONS

Kenichiro Shibata, Masayoshi Oga, Kazuo Hayashi, Yoichi Sugioka, "A New Contrivance of Anterior Spinal Fusion in Cervical Spine," *Orthopaedic and Traumatic Surgery*, vol. 35, No. 3, pp. 811–813, 1987.

Haruo Tsuji, "Anterior Body Fusion of Lumbar Spine Hernia," *Operation*, vol. 41, No. 11, pp. 1803–1811, 1987.

Hirotugu Oda, Shinya Kawai, Tetsuro Murakami, et al., "Osteoplastic Hemi/Bilateral Partial Laminectomy of Lumbar Spinal Hernia," *Operation*, vol. 41, No. 11, pp. 1785–1791, 1987.

Teiji Yano, et al., "Treatment of Spondylolisthesis By Posterior Fusion With Bone Grafting To Neural Arch Defect," *Clinical Orthopaedic Surgery*, vol. 17, No. 4, pp. 394–399, 1982.

Toshihiko Yamane, et al., "A Case Report of Multiple Lumbar Spondylolyses With Spondylolisthesis," *Clincal Orthopaedic Surgery*, vol. 23, No. 3, pp. 311–314, 1988.

M. Maeshiro, K. Otani, K. Shibasaki, S. Nakai, K. Nemoto, M. Yoshida, "Posterior Fracture–Dislocation of the Thoracic Spine: Two Cases Report," *Orthopedic Surgery*, vol. 39, No. 9, pp. 1373–1377, 1988–1989.

Kunio Takaoka, "Clinical Application of Ceramic Implants in Orthopedics Surgery," *Medicine Philosophica*, vol. 4, No. 7, pp. 546–552, 1985.

Y. Yamano, Y. Mikawa, R. Watanabe, et al., "Anterior Body Fusion of Lumbar Degenerative Spondylolisthesis," *Journal of the Western Japanese Research Society For Spine*, vol. 13, pp. 46–50.

"Dual Chisel and Its Bank Bones (Skimud Subkortikale Bones) For Posterior Lumbar Interbody Fusion—In Order To Simplify and Regularize the Surgical Procedure", *Orthopaedic Surgery*, vol. 11, pp. 150–153.

"Vertebral Body Distraction System (Caspar)," *Orthopaedic Surgery*, vol. 11, pp. 135–139.

Takayoshi Ueda, et al., "Instrumentation Surgery of Lumbar Interbody Fusion," *Central Japan Journal of Orthopaedic & Traumatic Surgery*, pp. 87–89.

Haruo Tsuji, et al., "Development and Clinical Application of Artificial Intervertebral Disc For Cervical Disc Lesions," *Central Japan Journal of Orthopaedic & Traumatic Surgery*, pp. 1505–1506.

"Intervertebral Body Fusion By The Use of Posterior Bone Dowel", by Benjamin R. Wiltberger, M.D., Clinical Orthopaedics, 35:69–79, 1964.

"Methods of Lumbar Fusion", by Norman W. Hoover, M.D., The Journal of Bone and Joint Surgery, vol. 50–A, No. 1, Jan. 1968 (pp. 194–210).

"Gewebsreaktion auf ein Titan–Hohlzylinderimplantat mit Titan–Spritzschichtoberfläche", by A. Schroeder, O. Pohler and F. Sutter, Separatdruck aus: Schweiz. Mschr. Zahnheilk. vol. 86, No. 7, pp. 713–727, 1976.

"Osseointegrated Titanium Implants, Requirements for Ensuring a Long–Lasting, Direct Bone–to–Implant Anchorage in Man", by T. Albrektsson et al., Acta orthop. scand. vol. 52, pp. 155–170, 1981.

"The Reactions of Bone, Connective Tissue, and Epithelium to Endosteal Implants With Titanium–Sprayed Surfaces", by Andre Schroeder et al., J.max.–fac.Surg. 9, pp. 15–25, 1981.

"Neue Rekonstruktionsmöglichkeiten bei Unterkieferdefekten nach Tummorresektion", by J. Raveh et al., Separatdruck aus: Schweiz. Mschr. Zahnheilk. vol. 91, Nr. 11, pp. 899–920, 1981.

"Cementless Fixation of Polyethylene Acetabular Component in Total Hip Arthroplasty", by E. W. Morscher et al., Archives of Arthopaedic and Taumatic Surgery, vol. 99, Issue 4, pp. 233–230, 1982.

"Neue Rekonstruktionsmöglichkeiten des Unterkiefers bei knöchernen Defekten nach Tumorresektionen", by J. Raueh et al., Chirurg, vol. 53, pp. 459–467, 1982.

"New Concepts in the Reconstruction of Mandibular Defects Following Tumor Resection", by Y. Reveh, M.D., DMD, et al., J Oral Maxillofax Surg, vol. 41, Issue 1, p. 3–16, Jan. 1983.

"Cervical Vertebral Interbody Fusion In The Horse: A Comparative Study Of Bovine Xenografts And Autografts Supported By Stainless Steel Baskets", by R. M. DeBowes et al., 29th Annual ORS, Anaheim, California, Mar. 8–10, 1983, p. 407 and 1 page of figures.

"Percutaneous Lateral Discectomy of the Lumbar Spine", by Parviz Kambin, M.D. et al., Clinical Orthopaedics, vol. 174, pp. 127–131, Apr., 1983.

"Anterior Discectomy and Interbody Fusion for Lumbar Disc Herniation", by Shun–Ichi Inque, M.D., Ph.D. et al., Clinical Orthopaedics and Related Research, No. 183, pp. 22–31, Mar. 1984.

"Use of the Titanium Coated Hollow Screw and Reconstruction Plate System In Bridging Lower Jaw Defects", by J. Raveh, et al., J Oral Maxillofac Surg., vol. 42, Issue 5, pp. 281–294, May 1984.

"Titanplasma–beschichtetes Holschrauben– und Rekonstruktions–platten–System (THRP) zur Überbrückung von Kieferdefekten", by F. Sutter et al., Chirurg, vol. 55, Issue 1, pp. 741–748, Nov. 1984.

"Titanplasma–beschichtetes Hohlschrauben– und Rekonstruktionsplatten–System (THRP) zur Überbrückung von Kieferdefekten", by F. Sutter et al., Chirurg, vol. 56, Issue 5, pp. 337–344, May 1985.

"Anterior Cervical Interbody Fusion With Threaded Cylindrical Bone", by Jose M. Otero Vich, M.D., J. Neurosurg, vol. 63, pp. 750–753, Nov., 1985.

"Die vordere Verplattung der Halswirbelsäule mit dem Hohlschrauben–Plattensystem aus Titanium", by E. Morscher et al., Chirurg, vol. 57, Issue 11, pp. 702–707, 1986.

"Surgical Procedures for Reconstruction of the Lower Jaw Using the Titanium–Coated Hollow–Screw Reconstruction Plate System: Bridging of Defects", by J. Raveh et al., The Otolaryngologic Clinics of North America, vol. 20, No. 3, pp. 535–558, Aug., 1987.

"Titanium Coated Hollow Screw and Reconstruction Plate System For Bridging Of Lower Jaw Defects: Biomechanical Aspects", by F. Sutter et al., Int. J. Oral Maxillofac. Surg., vol. 17, Issue 4, pp. 267–274, 1988.

"Arthrodesis By The Distraction–Compression Method Using A Stainless Steel Implant", by George W. Bagby, M.D., M.S., Orthopedics, vol. 11, pp. 931–934, Jun. 1988.

"Engineering and Design Aspects of the I.T.I. Hollow–Basket Implants", by F. Sutter, D.D.S. et al., Journal of Oral Implantology, pp. 535–551, 1983.

American Journal of Veterinarian Research, Author: Unknown, vol. 45, No. 1, Jan. 1984, pp. 195–199.

"Posterior Lumbar Interbody Fusion Made Simple", by G. M. Sava, Neurological Surgery Associates of Cincinnati, Inc., 2 pages, undated.

Surgical Titanium Mesh Ordering Information, DePuy Motech, Warsaw, Indiana, U.S.A., 2 pages, undated.

Cage CH—Lumbar spacing cages. SCIENT'X, Paris, France, 4 pages, undated.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 6, lines 42–61:

The fusion basket 10 of FIG. 1 was formed from a solid steel cylinder by drilling eight small, equally spaced holes 11 in the axial direction, each hole being centered on a circle concentric with the axis of the cylinder. Then a large hole was drilled centered on the axis and having a radius substantially identical to that of the aforementioned circle. *The drilling of the large hole in the cylinder creates a cage body wall 19.* A V-thread 12 *with flank 21* was then machined in the external surface of the cylinder, thus opening through that surface a perforation 13 extending through the rounded valley 14 of the V-thread at each crossing of the valley and one of the small holes 11. *At the perforation 13 the external surface tapers toward the internal surface and the V-thread 12 has a base 20.* A screw thread 15 was then machined in the internal surface of the fusion basket to threadably receive an end cap 16 that has apertures 18 similar to those of a salt shaker. Snap-on end caps would also be useful.

In making a fusion basket by the technique described in the preceding paragraph, the small holes 11 could be enlarged to intersect each other, thus making it unnecessary to drill a central hole. Enlarged small holes would result in larger perforations 13 *that are elongated along the direction of travel of the thread 12.*

THE DRAWING FIGURES HAVE BEEN CHANGED AS FOLLOWS:

Reference numerals 19, 20 and 21 have been added to FIG. 1.

AS A RESULT OF REEXAMINATION, IT HAS BEEN DETERMINED THAT:

Claims 1, 4, 6, 23 and 27–34 are determined to be patentable as amended.

Claims 2, 3, 5, 7–22 and 24–26, dependent on an amended claim, are determined to be patentable.

New claims 35–164 are added and determined to be patentable.

1. A fusion cage adapted for promoting fusion with [one or more] bone structures when bone-growth-[inducting]*inducing* substance is packed into the fusion cage, comprising:

a cage body defining an internal cavity adapted to be packed with the bone-growth-inducing substance, which cage body [defining] *defines* an outer surface;

means defined on the outer surface of the cage body for mating the fusion cage to the bone structure, which means prevents the fusion cage from backing out from the bone structure;

means for providing immediate contact between the [one or more bone] structures and the bone-growth-inducing substance packed into the fusion cage when the fusion cage is mated to the [one or more] bone structures so that the [one or more bone] structures cross over the outer surface into the internal cavity and into [the] contact with the bone-growth-inducing substance packed in the fusion cage.

4. The fusion cage of claim 1 wherein:

said mating means including a thread with a plurality of turns, and with valleys defined between said turns; and said means for providing immediate contact including a plurality of channels which communicate with said internal cavity, which channels define an inner surface and which channels pierce through the valleys to define a plurality of perforations whereby the inner surface contacts the outer surface, such channels also adapted to be packed with bone-growth-inducing substance so that there is immediate contact between the [one or more] bone structures and the bone-growth-inducing substance.

6. The fusion cage of claim 1:

wherein said cage body includes a helical structure [with an] *which includes said* outer surface and which helical structure has an inner surface, which inner surface defines said internal cavity;

said outer surface of the helical structure being substantially V-shaped and adapted for biting into the [one or more bone] structures; and said helical structure defining a plurality of spaced turns communicating with the internal cavity so that the inner surface contacts the outer surface such that with the outer surface biting into the bone structure, there is immediate contact between the [one or more] bone structures and with the bone-growth-inducing substance packed into the internal cavity of the fusion cage.

23. The fusion cage as defined in claim 7 wherein the V-thread [are] *is* substantially sharp [with] *and* the valleys are substantially rounded.

27. A fusion cage adapted for promoting fusion with [one or more] bone structures when bone-growth-inducing substance is packed into the fusion cage, comprising:

a cage body having an inner surface which defines a cavity adapted to be packed with the bone-growth-inducing substance;

said cage body defining an outer surface;

means defined on the outer surface of the cage body adapted for allowing the fusion cage to bite into the bone structure;

means for providing a plurality of [sites] *perforations at a portion* where the inner surface contacts the outer surface *so that the perforations have no substantial depth* in order to allow immediate contact between the [one or more] bone structures and the bone-growth-inducing substance packed into the fusion cage.

28. A fusion cage adapted for promoting fusion of [one or more] bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting in the bone structure;

said threads defining means including a plurality of threads which define valleys therebetween;

a plurality of perforations provided in the valleys of the threads for providing communication between the outer surface and the cavity in order to allow immediate contact between the [one or more] bone structures and the bone-growth-inducing substance packed into the fusion cage.

29. A fusion cage adapted for promoting fusion with [one or more] bone structures when bone-growth-inducing substance is packed into the fusion cage, comprising:

a cage body defining a cavity with an inner surface, said cavity adapted to be packed with bone-growth-inducing substance;

said cage body defining an outer surface comprised of a substantially continuous thread with a plurality of turns and valleys defined between said turns;

a plurality of perforations defined in said valleys so that the inner surface contacts the outer surface in order to allow immediate contact between the [one or more] bone structures and the bone-growth-inducing substance packed into the fusion cage.

30. A fusion cage adapted for promoting the fusion with [one or more] bone structures when bone-growth-inducing substance is packed into the fusion cage comprising:

a cage body defining a cavity with an inner surface, the cavity being adapted to be packed with bone-growth-inducing substance;

said cage body defining an outer surface comprised of a substantially continuous thread with a plurality of turns and valleys defined between adjacent turns;

said cavity defining a plurality of channels which pierce through the valleys to define a plurality of perforations whereby the inner surface contacts the outer surface so that there is immediate contact between the [one or more] bone structures and the bone-growth-inducing substance packed into the fusion cage.

31. A fusion cage adapted for promoting fusion with [one or more bone] structures when bone-growth-inducing substance is packed into the fusion cage comprising:

a plurality of spaced elongate members which define an internal cavity;

said elongate members having an inner surface that faces the internal cavity and an outer surface that faces away from the internal cavity;

a helical thread member formed about and connected to the outer surfaces of the spaced elongate members, which helical thread member defines a plurality of turns; and a plurality of apertures defined between turns, which apertures are bordered by the spaced elongate member, wherein the thread member is adapted to contact between the [one or more] bone structures and the bone-growth-inducing substance packed into the fusion cage.

32. A fusion cage adapted for promoting the fusion with [one or more] bone structures when bone-growth-inducing substance is packed into the fusion cage, comprising:

a helical structure having an inner surface which defines an internal cavity;

said helical structure having a substantially V-shaped outer surface pointing in a direction away from the internal cavity and adapted for biting into the [one or more] bone structures;

said helical structure defining a plurality of spaced turns communicating with the internal cavity so that the inner surface intersects the outer surface *forming perforations only between the turns* such that with the outer surface biting into the [one or more] bone structures, there is immediate contact between the [one or more] bone structures and the bone-growth-inducing substance packed into the internal cavity of the fusion cage.

33. A surgical method for fusing a fusion cage with [one or more] bone structures comprising the steps of:

forming a bore with an internal thread, in the [one or more] bone structures;

screwing the fusion cage into the bore which fusion cage includes:

(a) a cage body defining an internal cavity with an inner surface, and the cage body having an outer surface defining an external thread that mates with the internal thread, the external thread having a plurality of adjacent turns which define valleys therebetween; and (b) a multiplicity of perforations located in the valleys in such a manner that the inner surface [contact] *contacts* the outer surface;

said screwing step further causing the [one or more] bone structures to extend through the perforations and into the internal cavity;

packing the fusion cage with bone-growth-inducing substance in such a manner that the bone-growth-inducing substance contacts the [one or more] bone structures and the outer surface.

34. A fusion cage adapted for promoting the fusion with [one or more] bone structures when bone-growth-inducing substance is packed into the fusion cage, comprising:

a helical structure having an inner surface which defines an internal cavity;

said helical structure having an outer surface pointing in a direction away from the internal cavity and adapted for contacting [one or more] bone structures;

said helical structure defining a plurality of spaced turns communicating with the internal cavity, *and forming perforations only between the turns,* such that with the outer surface contacting the [one or more] bone structures there is immediate contact between the [one or more] bone structure and the bone-growth-inducing substance packed into the internal cavity of the fusion cage.

*35. The fusion cage of claim 2 wherein the cage body has a diameter of about twelve millimeters to about sixteen millimeters and the cage body has a length of about twenty millimeters to about twenty-five millimeters.*

*36. The fusion cage of claim 4 wherein:*

*said channels intersect each other in order to define the inner surface of said internal cavity.*

*37. The fusion cage of class 36 wherein:*

*said thread has a crown and a flank located between the crown and the valleys; and*

*said perforations are formed with the channels piecing through the flank of the thread.*

*38. The fusion cage of claim 4 wherein:*

*said thread has a crown and a flank located between the crown and the valleys; and*

*said perforations are formed with the channels piercing through the flank of the thread.*

39. The fusion cage of claim 1, wherein the cage body has a diameter of about 12 mm to about 16 mm and the cage body has a length of about 20 mm to about 25 mm.

40. The fusion cage of claim 27 wherein the cage body has a diameter of about twelve millimeters to about sixteen millimeters and the cage body has a length of about twenty millimeters to about twenty-five millimeters.

41. The fusion cage of claim 28, wherein the cage body has a diameter of about 12 mm to about 16 mm and the cage body has a length of about 20 mm to about 25 mm.

42. The fusion cage of claim 28 wherein the cage body has a length of from about twenty millimeters to about twenty-five millimeters.

43. The fusion cage of claim 28 wherein the cage body has a diameter which is from twelve millimeters to sixteen millimeters.

44. The fusion cage of claim 29 wherein the cage body has a diameter of about twelve millimeters to about sixteen millimeters and the cage body has a length of about twenty millimeters to about twenty-five millimeters.

45. The fusion cage of claim 28 wherein the cage body has a diameter of from about twelve millimeters to about sixteen millimeters.

46. The fusion cage of claim 30 wherein the cage body has a diameter of about twelve millimeters to about sixteen millimeters and the cage body has a length of about twenty millimeters to about twenty-five millimeters.

47. The fusion cage of claim 32 wherein:

said perforations are elongated along the direction of travel of said helical structure.

48. The fusion cage of claim 32 wherein the cage body has a diameter of about twelve millimeters to about sixteen millimeters and the cage body has a length of about twenty millimeters to about twenty-five millimeters.

49. The fusion cage of claim 34, wherein the helical structure has a diameter of about 12 mm to about 16 mm and the helical structure has a length of about 20 mm to about 25 mm.

50. The fusion cage of claim 34 wherein:

said perforations are elongated along the direction of travel of said helical structure.

51. A fusion cage adapted for promoting fusion with bone structures when bone-growth-inducing substance is packed into the fusion cage, comprising:

a cage body defining an internal cavity adapted to be packed with the bone-growth-inducing substance, which cage body defines an outer surface;

means defined on the outer surface of the cage body for mating the fusion cage to the bone structure, which means prevents the fusion cage from backing out from the bone structure; and means for providing immediate contact between the bone structures and the bone-growth-inducing substance packed into the fusion cage when the fusion cage is mated to the bone structures so that the bone structures cross over the outer surface of the cage body and project into the internal cavity and into contact with the bone-growth-inducing substance packed in the fusion cage.

52. The fusion cage of claim 51 wherein said internal cavity of said cage body defines an inner surface, and wherein the cage body has a cage body wall; and wherein said means for providing immediate contact includes a plurality of sites where the inner surface meets the outer surface without the cage body wall spacing the inner surface from the outer surface, at said plurality of sites.

53. The fusion cage of claim 51 wherein said internal cavity of said cage body defines an inner surface and wherein the cage body has a cage body wall;

wherein said mating means includes a thread with a plurality of turns and with valleys defined between said turns; and wherein said means for providing immediate contact includes a plurality of perforations defined in said valleys so that the inner surface contacts the outer surface without the cage body wall spacing the inner surface from the outer surface, at said plurality of perforations.

54. The fusion cage of claim 51:

wherein said cage body has a helical structure which includes said outer surface and which helical structure has an inner surface, which inner surface defines said internal cavity;

said outer surface of the helical structure being adapted for biting into the bone structures; and said helical structure defining a plurality of spaced turns communicating with the internal cavity so that the inner surface contacts the outer surface such that with the outer surface biting into the bone structures, there is immediate contact between the bone structures, there is immediate contact between the bone structures and the bone-growth-inducing substance packed into the internal cavity of the fusion cage.

55. The fusion cage of claim 51 wherein:

said outer surface defines an external thread adapted for mating to the bone structure;

which thread has a multiplicity of turns and valleys defined between said turns; and said means for providing immediate contact includes a multiplicity of perforations located in said valleys that provide communication between said said outer surface and said internal cavity.

56. A fusion cage as defined in claim 55 wherein the thread has a angle at the crown of the thread that is not more than 90°, but not less than 45°.

57. A fusion cage as defined in claim 55 wherein the angle at the crown of the thread is about 60°.

58. A fusion cage as defined in claim 55 wherein the thread has from about 3 to about 8 turns per cm.

59. A fusion cage as defined in claim 55 wherein the valleys of the thread have fillets, the radius of which is from 0.35 mm to 0.75 mm.

60. A fusion cage as defined in claim 55 wherein, the internal cavity defines an inner surface and wherein said perforations comprise at least from about 30% to about 60% of said inner surface.

61. A fusion cage as defined in claim 51 which is fitted with a removable perforated end cap.

62. A fusion cage as defined in claim 51, wherein a major diameter of which is from about 12 mm to about 16 mm.

63. The fusion cage as defined in claim 51 wherein said means for providing immediate contact is substantially uniformly distributed throughout the outer surface of the cage body.

64. The fusion cage as defined in claim 51, which has a length of about 20 mm to about 25 mm.

65. A fusion cage adapted for promoting fusion with bone structures when bone-growth-inducing substance is packed into the fusion cage, comprising:

a cage body defining an internal cavity adapted to be packed with the bone-growth-inducing substance, which cage body defines an outer surface;

means defined on the outer surface of the cage body for mating the fusion cage to the bone structure, which means prevents the fusion cage from backing out from the bone structure; and means for providing immediate contact between the bone structures and the bone-growth-inducing substance packed into the fusion cage so that immediately upon insertion of the fusion cage into the bone structures, the bone structures cross over the outer surface into the internal cavity and into contact with the bone-growth-inducing substance when such bone-growth-inducing substance is packed in the fusion cage.

66. A fusion cage adapted for promoting fusion with bone structures when bone-growth-inducing substance is packed into the fusion cage, comprising:

a cage body defining an internal cavity adapted to be packed with the bone-growth-inducing substance, which cage body defining an outer surface;

means defined on the outer surface of the cage body for mating the fusion cage to the bone structure, which means prevents the fusion cage from backing out from the bone structure;

means for providing immediate contact between the bone structures and the bone-growth-inducing substance packed into the fusion cage when the fusion cage is mated to the bone structures so that the bone structures cross over the outer surface into the internal cavity and into the contact with the bone-growth-inducing substance packed in the fusion cage;

said mating means including a thread with a plurality of turns, and with valleys defined between said turns and said internal cavity defines an inner surface; and said means for providing immediate contact including said inner surface piercing through only the valleys to define a plurality of perforations.

67. The fusion cage of claim 66 wherein:

at said perforations said inner surface contacts the outer surface so that there is immediate contact between the one or more bone structures and bone-growth-inducing substance packed in the internal cavity.

68. A fusion cage adapted for promoting fusion with bone structures when bone-growth-inducing substance is packed into the fusion cage, comprising:

a cage body defining an internal cavity adapted to be packed with the bone-growth-inducing substance, which cage body defining an outer surface;

means defined on the outer surface of the cage body for mating the fusion cage to the bone structure, which means prevents the fusion cage from backing out from the bone structure;

means for providing immediate contact between the bone structures and the bone-growth-inducing substance packed into the fusion cage when the fusion cage is mated to the bone structures so that the bone structures cross over the outer surface into the internal cavity and into the contact with the bone-growth-inducing substance packed in the fusion cage;

said mating means including a thread with a plurality of turns, and with valleys defined between said turns and said internal cavity defines an inner surface; and said means for providing immediate contact including said inner surface piercing throug only the valleys to define a plurality of perforations; and wherein the thread has a crown and the perforations are located in the valleys of the thread without interrupting the crown of the thread.

69. The fusion cage of claim 66 wherein the perforations are located in the valleys of the thread without interrupting a crown of the thread.

70. A fusion cage adapted for promoting fusion with bone structures when bone-growth-inducing substance is packed into the fusion cage, comprising:

a cage body defining an internal cavity adapted to be packed with the bone-growth-inducing substance, which cage body defining an outer surface;

means defined on the outer surface of the cage body for mating the fusion cage to the bone structure, which means prevents the fusion cage from backing out from the bone structure;

means for providing immediate contact between the bone structures and the bone-growth-inducing substance packed into the fusion cage when the fusion cage is mated to the bone structures so that the bone structures cross over the outer surface into the internal cavity and into the contact with the bone-growth-inducing substance packed in the fusion cage;

wherein said means for providing immediate contact includes a plurality of perforations located in said cage body;

wherein the internal cavity defines an inner surface; and wherein said perforations comprise at least from about 30% to about 60% of said inner surface.

71. The fusion cage of claim 70 wherein:

said outer surface defines an external thread adapted for mating to the bone structure;

said thread has a multiplicity of turns and valleys defined between said turns; and said perforations are located in said valleys and provide communication between said outer surface and said internal cavity.

72. A fusion cage adapted for promoting fusion with bone structures when bone-growth-inducing substance is packed into the fusion cage, comprising:

a cage body having an inner surface which defines a cavity adapted to be packed with the bone-growth-inducing substance and wherein said cage body has a cage body wall;

said cage body defining an outer surface;

means defined on the outer surface of the cage body adapted for allowing the fusion cage to bite into the bone structure;

means for providing a plurality of sites where the inner surface contacts the outer surface, without the cage body wall spacing the inner surface from the outer surface, at the plurality of sites, in order to allow immediate contact between the bone structures and the bone-growth-inducing substance packed into the fusion cage.

73. The fusion cage of claim 72 wherein:

said means for allowing the fusion cage to bite into the bone structure includes a thread with turns and a valley located between the turns, the thread having a crown and a flank located between the crown and the valley; and said plurality of sites are formed with said inner surface piercing through the flank of the thread.

74. The fusion cage of claim 72 wherein:

said means for allowing the fusion cage to bite into the bone structure includes a thread with turns and a valley located between the turns; and said plurality of sites are formed with said inner surface piercing through the valley of the thread.

75. A fusion cage adapted for promoting fusion of bone structures when bone-growth-inducing substance is packed into the fusion cage, comprising:
  a cage body defining a cavity with an inner surface, said cavity adapted to be packed with the bone-growth-inducing substance;
  said cage body defining an outer surface;
  means for defining threads on the outer surface of the cage body and adapted for biting into the bone structure;
  said threads defining means including a plurality of threads which define valleys therebetween;
  a plurality of perforations provided in the valleys of the threads for providing communication between the outer surface and the cavity in order to allow immediate contact between the bone structures and the bone-growth-inducing substance packed into the fusion cage; and
  wherein said inner surface of said cavity pierces through the valleys in order to define the plurality of perforations such that said perforations have no substantial depth.

76. The fusion cage of claim 75 wherein:
  said cage body has a cage body wall; and
  wherein said inner surface contacts the outer surface at said plurality of perforations without the cage body wall spacing the inner surface from the outer surface.

77. The fusion cage of claim 75 wherein:
  said threads have crowns; and
  said inner surface pierces through the valleys without interrupting the crowns.

78. A fusion cage adapted for promoting fusion of bone structures when bone-growth-inducing substance is packed into the fusion cage, comprising:
  a cage body defining a cavity with an inner surface, said cavity adapted to be packed with the bone-growth-inducing substance;
  said cage body defining an outer surface;
  means for defining threads on the outer surface of the cage body and adapted for biting into the bone structure;
  said threads defining means including a plurality of threads which define valleys therebetween;
  a plurality of perforations provided in the valleys of the threads for providing communication between the outer surface and the cavity in order to allow immediate contact between the bone structures and the bone-growth-inducing substance packed into the fusion cage;
  wherein said inner surface of said cavity pierces through the valleys in order to define the plurality of perforations;
  wherein said threads have crowns and flanks located between the crowns and the valleys; and
  wherein said plurality of perforations are formed with the inner surface piercing through only the flanks and only the valleys of the threads.

79. A fusion cage adapted for promoting fusion of bone structures when bone-growth-inducing substance is packed into the fusion cage, comprising:
  a cage body defining a cavity with an inner surface, said cavity adapted to be packed with the bone-growth-inducing substance;
  said cage body defining an outer surface;
  means for defining threads on the outer surface of the cage body and adapted for biting into the bone structure;
  said threads defining means including a plurality of threads which define valleys therebetween;
  a plurality of perforations provided in the valleys of the threads for providing communication between the outer surface and the cavity in order to allow immediate contact between the bone structures and the bone-growth-inducing substance packed into the fusion cage;
  wherein said inner surface of said cavity pierces through the valleys in order to define the plurality of perforations;
  said threads have substantially continuous crowns; and
  said inner surface pierces through said valleys without substantially interrupting the substantially continuous crown.

80. A fusion cage adapted for promoting fusion with bone structures when bone-growth-inducing substance is packed into the fusion cage comprising:
  a cage body defining a cavity with an inner surface, the cavity being adapted to be packed with bone-growth-inducing substance;
  said cage body defining an outer surface comprised of a substantially continuous thread with a plurality of turns and valleys defined between adjacent turns and with a substantially continuous crown;
  said cavity defining a plurality of channels which pierce through the valleys to define a plurality of perforations whereby the inner surface contacts the outer surface so that there is immediate contact between the bone structures and the bone-growth-inducing substance packed in to the fusion cage; and
  wherein said channels pierce through said valleys without substantially interrupting the substantially continuous crown of said thread.

81. The fusion cage of claim 81 wherein said channels intersect each other in order to define the inner surface of said cavity.

82. A fusion cage adapted for promoting the fusion with bone structures when bone-growth-inducing substance is packed into the fusion cage, comprising:
  a helical structure having an inner surface which defines an internal cavity;
  said helical structure having a substantially V-shaped outer surface pointing in a direction away from the internal cavity and adapted for biting into the bone structures, with the inner surface defined by the base of the V-shaped outer surface;
  said helical structure defining a plurality of spaced turns communicating with the internal cavity so that the inner surface intersects the outer surface at the base of the V-shaped outer surface such that with the outer surface biting into the bone structures, there is immediate contact between the bone structures and the bone-growth-inducing substance packed into the internal cavity of the fusion cage.

83. A fusion cage adapted for promoting fusion with bone structures when bone-growth-inducing substance is packed into the fusion cage, comprising:
  a helical structure having an inner surface which defines an internal cavity;
  said helical structure having an outer surface pointing in a direction away from the internal cavity and adapted for contacting bone structures;

said helical structure defining a plurality of spaced turns (1) which communicate with the internal cavity and (2) which allows the bone structures to cross over the outer surface and project into the internal cavity and into contact the bone-growth-inducing substance packed in the fusion cage, such that with the outer surface contacting the bone structures, there is immediate contact between the bone structures and the bone-growth-inducing substance packed into the internal cavity of the fusion cage.

84. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and wherein at least some of the perforations are from about 1 mm in dimension both axially and transversely along the direction of said threads to about 2 mm axially and about 3 mm transversely along the direction of said threads in dimension to permit good ingrowth of bone and so as not to unduly weaken the cage.

85. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys between turns of the threads;

a plurality of perforations provided in the valleys between turns of the threads for providing communication between the outer surface and the cavity in order to allow immediate contact between the bone structures and the bone-growth-inducing substance packed into the fusion cage;

wherein the threads have crowns and flanks located between the crowns and valleys; and wherein at least some of the perforations are each located in only one valley located between adjacent turns and with said at least some of said perforations also extending into one or both of the flanks of said adjacent turns.

86. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys between turns of the threads;

a plurality of perforations provided in the valleys between turns of the threads for providing communication between the outer surface and the cavity in order to allow immediate contact between the bone structures and the bone-growth-inducing substance packed into the fusion cage;

wherein the threads have crowns and flanks located between the crowns and valleys; and wherein at least some of the perforations are each formed in only one valley located between adjacent turns and with said at least some of said perforations also extending into one or both of the flanks of said adjacent turns.

87. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys between turns of the threads;

a plurality of perforations provided in the valleys between turns of the threads for providing communication between the outer surface and the cavity in order to allow immediate contact between the bone structures and the bone-growth-inducing substance packed into the fusion cage;

wherein the threads have crowns and flanks located between the crowns and valleys; and wherein at least some of the perforations are each located in only one valley located between adjacent turns and with said at least some of said perforations also extending across the valley from about the flank of one turn to about the flank of an adjacent turn.

88. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and wherein said perforations comprise at least from about 30% to about 60% of said inner surface.

89. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and which cage body is fitted with a removable perforated end cap.

90. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and wherein a major diameter of the cage body is from about 12 mm to about 16 mm.

91. The fusion cage of claim 90 which has a length of about 20 mm to about 25 mm and there are from about 3 to about 8 threads per cm.

92. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

said cage body having a major diameter from about 12 mm to about 16 mm;

means for defining threads on the outer surface of the cage body and adapted for biting into the bone structure;

said threads defining means including a plurality of threads which define valleys therebetween, the threads defining turns with about from 3 turns per cm to about 8 turns per cm;

a plurality of perforations provided in the valleys of the threads for providing communication between the outer surface and the cavity in order to allow immediate contact between the bone structures and the bone-growth-inducing substance packed into the fusion cage;

wherein said perforations comprise at least from about 30% to about 60% of said inner surface.

93. The fusion cage of claim 92 wherein the cage body has a length of about 20 mm to about 25 mm.

94. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance, which cage body defines an outer surface;

said cage body having a major diameter from about 12 mm to about 16 mm;

means defined on the outer surface of the cage body for mating the fusion cage on the bone structure, which means prevents the fusion cage from backing out from the bone structure, said mating means including a thread;

said thread defining valleys and turns with from about 3 turns per cm to about 8 turns per cm;

means for providing immediate contact between the bone structures and the bone-growth-inducing substance packed into the fusion cage when the fusion cage is mated to the bone structures so that the bone structures cross over the outer surface into the internal cavity and into contact with the bone-growth-inducing substance packed in the fusion cage;

said means for providing immediate contact, including a plurality of perforations provided in the valleys of the thread; and wherein said perforations comprise at least from about 30% to about 60% of said inner surface.

95. The fusion cage of claim 94 wherein the cage body has a length about 20 mm to about 25 mm.

96. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage;

wherein said perforation comprise about 25% of said inner surface.

97. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage;

said threads having continuous crowns; and said perforations are provided in said valleys without interrupting the continuous crown.

98. A fusion cage adapted for promoting fusion of bone structures when bone-growth-inducing substance is packed into the fusion cage, comprising:

a cage body defining an internal cavity adapted to be packed with the bone-growth-inducing substance which cage body defining an outer surface;

means defined on the outer surface of the cage body for mating the fusion cage to the bone structure, which means prevents the fusion cage from backing out from the bone structure;

means for providing immediate contact between the bone structures and the bone-growth-inducing substance packed into the fusion cage when the fusion cage is mated to the bone structures so that the bone structures cross over the outer surface into the internal cavity and into the contact with the bone-growth-inducing substance packed in the fusion cage;

said outer surface defines a V-thread adapted for mating to the bone structure;

which thread has a multiplicity of turns and valleys defined between said turns; and wherein the V-thread is substantially sharp and the valleys are substantially rounded.

99. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage;

wherein the threads are substantially sharp and the valleys are substantially rounded.

100. A fusion cage adapted for promoting fusion of bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity such that with the outer surface contacting the bone structures and the bone-growth-inducing substance packed into the internal cavity of the fusion cage;

said outer surface defines a V-thread adapted for mating to the bone structure; and the V-thread is substantially sharp and the valleys are substantially rounded.

101. A fusion cage adapted for promoting fusion of bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity such that with the outer surface contacting the bone structures, there is immediate contact between the bone structures and the bone-growth-inducing substance packed into the internal cavity of the fusion cage;

said helical structure having valleys defined between said turns; and said inner surface pierces through only the valleys to define a plurality of perforations whereby the inner surface contacts the outer surface.

102. A fusion cage adapted for promoting fusion of bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity such that with the outer surface contacting the bone structures, there is immediate contact between the bone structures and the bone-growth-inducing substance packed into the internal cavity of the fusion cage;

said helical structure has valleys defined between said turns;

said means for providing immediate contact includes a multiplicity of perforations located in said valleys that provide communication between said outer surface and said internal cavity; and wherein said perforations comprised at least from about 30% to about 60% of said inner surface.

103. A fusion cage adapted for promoting fusion of bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity such that with the outer surface contacting the bone structures, there is immediate contact between the bone structures and the bone-growth-inducing substance packed into the internal cavity of the fusion cage; and wherein said helical structure is fitted with a removable perforated end cap.

104. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage;

wherein the plurality of threads define turns and the fusion cage has from about 3 to about 8 turns per cm.

105. A fusion cage adapted for promoting fusion of bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity such that with the outer surface contacting the bone structures, there is immediate contact between the bone structures and the bone-growth-inducing substance packed into the internal cavity of the fusion cage; and wherein the helical structure has from about 3 to about 8 turns per cm.

106. A fusion cage adapted for promoting fusion of bone structures when bone-growth-inducing substance is packed into the fusion cage, comprising:

a cage body defining a cavity with an inner surface, said cavity adapted to be packed with bone-growth-inducing substance;

said cage body defining an outer surface comprised of a substantially continuous thread with a crown and with a plurality of turns and valleys defined between said turns;

a plurality of perforations defined in the valleys so that the inner surface contacts the outer surface in order to allow immediate contact between the bone structures and the bone-growth-inducing substance packed into the fusion cage; and wherein said perforations do not interrupt said crown of said substantially continuous thread.

107. A fusion cage adapted for promoting fusion of bone structures when bone-growth-inducing substance is packed into the fusion cage, comprising:

a cage body defining a cavity with an inner surface, said cavity adapted to be packed with bone-growth-inducing substance;

said cage body defining an outer surface comprised of a substantially continuous thread having a continuous crown and with a plurality of turns and valleys defined between said turns;

a first plurality of perforations defined in said valleys so that the inner surface contacts the outer surface in order to allow immediate contact between the bone structures and the bone-growth-inducing substance packed into the fusion cage and a second plurality of perforations defined in the cage body;

wherein said substantially continuous thread with the continuous crown extends with multiple turns through said first plurality of perforations.

108. A fusion cage adapted for promoting fusion with bone structures, comprising:

a cage body defining an internal cavity and an outer surface;

a bone-growth-inducing substance packed into the internal cavity;

means defined on the outer surface of the cage body for mating the fusion cage to the bone structure, which means prevents the fusion cage from backing out from the bone structure; and means for providing immediate contact between the bone structures and the bone-growth-inducing substance packed into the fusion cage when the fusion cage is mated to the bone structures so that the bone structures cross over the outer surface into the internal cavity and into contact with the bone-growth-inducing substance packed in the fusion cage.

109. The fusion cage of claim 108 wherein:

said fusion cage is to be implanted between two adjacent human vertebrae.

110. A fusion cage adapted for promoting fusion with bone structures, comprising:

a cage body having an inner surface which defines a cavity;

a bone-growth-inducing substance packed into the cavity;

said cage body defining an outer surface;

means defined on the outer surface of the cage body adapted for allowing the fusion cage to bite into the bone structure; and means for providing a plurality of sites where the inner surface contacts the outer surface in order to allow immediate contact between the bone structures and the bone-growth-inducing substance packed into the fusion cage.

111. The fusion cage of claim 110 wherein:

said fusion cage is to be implanted between two adjacent human vertebrae.

112. A fusion cage adapted for promoting fusion of bone structures, comprising:

a cage body defining a cavity with an inner surface;

a bone-growth-inducing substance packed into the cavity;

said cage body defining an outer surface;

means for defining threads on the outer surface of the cage body and adapted for biting into the bone structure;

said threads defining means including a plurality of threads which define valleys therebetween; and a plurality of perforations provided in the valleys of the threads for providing communication between the outer surface and the cavity in order to allow immediate contact between the bone structures and the bone-growth-inducing substance packed into the fusion cage.

113. The fusion cage of claim 112 wherein:

said fusion cage is to be implanted between two adjacent human vertebrae.

114. A fusion cage adapted for promoting fusion of bone structures, comprising:

a cage body defining a cavity with an inner surface;

a bone-growth-inducing substance packed into the cavity;

said cage body defining an outer surface comprised of a substantially continuous thread with a plurality of turns and valleys defined between said turns; and a plurality of perforations defined in said valleys so that the inner surface contacts the outer surface in order to allow immediate contact between the bone structures and the bone-growth-inducing substance packed into the fusion cage.

115. The fusion cage of claim 114 wherein:

said fusion cage is to be implanted between two adjacent human vertebrae.

116. A fusion cage adapted for promoting the fusion with bone structures, comprising:

a cage body defining a cavity with an inner surface;

a bone-growth-inducing substance packed into the cavity;

said cage body defining an outer surface comprised of a substantially continuous thread with a plurality of turns and valleys defined between adjacent turns; and said cavity defining a plurality of channels which pierce through the valleys to define a plurality of perforations whereby the inner surface contacts the outer surface so that there is immediate contact between the bone structures and the bone-growth-inducing substance packed into the fusion cage.

117. The fusion cage of claim 116 wherein:

said fusion cage is to be implanted between two adjacent human vertebrae.

118. A fusion cage adapted for promoting fusion with bone structures, comprising:

a helical structure having an inner surface which defines an internal cavity;

a bone-growth-inducing substance packed into the internal cavity;

said helical structure having a substantially V-shaped outer surface pointing in a direction away from the internal cavity and adapted for biting into the bone structures; and said helical structure defining a plurality of spaced turns communicating with the internal cavity so that the inner surface intersects the outer surface such that with the outer surface biting into the bone structures, there is immediate contact between the bone structures and the bone-growth-inducing substance packed into the internal cavity of the fusion cage.

119. The fusion cage of claim 118 wherein:

said fusion cage is to be implanted between two adjacent human vertebrae.

120. A fusion cage adapted for promoting fusion with bone structures, comprising:

a helical structure having an inner surface which defines an internal cavity;

a bone-growth-inducing substance packed into the internal cavity;

said helical structure having an outer surface pointing in a direction away from the internal cavity and adapted for contacting bone structures; and said helical structure defining a plurality of spaced turns communicating with the internal cavity such that with the outer surface contacting the bone structures, there is immediate contact between the bone structures and the bone-growth-inducing substance packed into the internal cavity of the fusion cage.

121. The fusion cage of claim 120 wherein:

said fusion cage is to be implanted between two adjacent human vertebrae.

122. A fusion cage for promoting fusion between human vertebrae, comprising:

a cage body having an outer surface and an internal cavity;

a bone-growth-inducing substance positioned in the internal cavity; and, said outer surface having threads, forming valleys, wherein a plurality of perforations are positioned in the valleys to allow immediate contact between the human vertebrae and the bone-growth-inducing substance.

123. The fusion cage of claim 122, wherein the thread has from about 3 turns per cm to about 8 turns per cm.

124. The fusion cage of claim 122, wherein the internal cavity defines an inner surface and a plurality of said perforation, said plurality of said perforation comprise at least from about 30% to about 60% of the inner surface.

125. The fusion cage of claim 122, wherein the fusion cage has a removable end cap.

126. The fusion cage of claim 122, wherein the major diameter length is from about 12 mm to about 16 mm and the axial length is from about 20 mm to about 25 mm.

127. The fusion cage of claim 122, wherein the perforation is positioned between a first turn and a second turn of the thread.

128. The fusion cage of claim 127, wherein the first turn and second turn are adjacent.

129. The fusion cage of claim 122, wherein the thread is V-shaped, having multiple turns, and the valley is formed between adjacent crowns of the V-shaped thread.

130. A fusion cage adapted for promoting fusion with bone structures when bone-growth-inducing substance is packed into the fusion cage, comprising:

a cage body defining an internal cavity adapted to be packed with the bone-growth-inducing substance, which cage body defines an outer surface;

means defined on the outer surface of the cage body for mating the fusion cage to the bone structure, which means prevents the fusion cage from backing out from the bone structure;

means for having the bone structures cross over the outer surface into the internal cavity and into contact with the bone-growth-inducing substance packed in the fusion cage for providing immediate contact between the bone structures and the bone-growth-inducing substance packed into the fusion cage with the fusion cage mated to the bone structures.

131. A fusion cage adapted for promoting fusion with bone structures when bone-growth-inducing substance is packed into the fusion cage, comprising;

a cage body having an inner surface which defines a cavity adapted to be packed with the bone-growth-inducing substance;

said cage body defining an outer surface;

means defined on the outer surface of the cage body adapted for allowing the fusion cage to bite into the bone structure;

means for providing a plurality of sites where the inner surface and the outer surface taper toward each other with the inner surface contacting the outer surface in order to allow immediate contact between the bone structures and the bone-growth-inducing substance packed into the fusion cage.

132. The fusion cage of claim 131 wherein at said plurality of perforations where the inner surface and the outer surface taper toward each other, the inner surface is disposed at less than a 90° angle to the outer surface.

133. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations, said perforations having no substantial depth and being provided in the valleys of the threads for providing communication between the outer surface and the cavity in order to allow immediate contact between the bone structures and the bone-growth-inducing substance packed into the fusion cage.

134. A fusion cage adapted for promoting fusion with bone structures when bone-growth-inducing substance is packed into the fusion cage, comprising:

a cage body defining a cavity with an inner surface, said cavity adapted to be packed with bone-growth-inducing substance;

said cage body defining an outer surface comprised of a substantially continuous thread with a plurality of turns and valleys defined between said turns;

a plurality of perforations, said perforations having no substantial depth and defined in said valleys so that the inner surface contacts the outer surface in order to allow immediate contact between the bone structures and the bone-growth-inducing substance packed into the fusion cage.

135. A fusion cage adapted for promoting the fusion with bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures with the inner surface defined by a base of the helical structure;

said helical structure defining a plurality of spaced turns communicating with the internal cavity so that the base intersect the outer surface at the turns of the helical structure such that with the outer surface contacting the bone structures, there is immediate contact between the bone structures and the bone-growth-inducing substance packed into the internal cavity of the fusion cage.

136. A fusion cage adapted for promoting fusion with bone structures when bone-growth-inducing substance is packed into the fusion cage, comprising:

a cage body defining an internal cavity adapted to be packed with the bone-growth-inducing substance, which cage body defines an outer surface;

means defined on the outer surface of the cage body for mating the fusion cage to the bone structure, which means prevents the fusion cage from backing out from the bone structure; and means for providing immediate contact between the bone structures and the bone-growth-inducing substance packed into the fusion cage with the fusion cage mated to the bone structures so that the bone structures cross over the outer surface of the cage body and project into the internal cavity and into contact with the bone-growth-inducing substance packed in the fusion cage.

137. A fusion cage adapted for promoting fusion with bone structures when bone-growth-inducing substance is packed into the fusion cage, comprising:

a cage body defining an internal cavity adapted to be packed with the bone-growth-inducing substance, which cage body defining an outer surface;

means defined on the outer surface of the cage body for mating the fusion cage to the bone structure, which means prevents the fusion cage from backing out from the bone structure;

means for providing immediate contact between the bone structures and the bone-growth-inducing substance packed into the fusion cage when the fusion cage is mated to the bone structures so that the bone structures cross over the outer surface into the internal cavity and into contact with the bone-growth-inducing substance packed in the fusion cage;

wherein said means for providing immediate contact includes a plurality of perforations located in said cage body;

wherein the internal cavity defines an inner surface; and wherein said perforations comprise at least from 30% to 60% of said inner surface.

138. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and wherein said inner surface of said cavity pierces through only the valleys in order to define the plurality of perforations.

139. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and wherein said perforations comprise at least from 30% to 60% of said inner surface.

140. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and which cage body is fitted with removable perforated end caps.

141. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

said cage body having a major diameter from about 12 mm to about 16 mm;

means for defining threads on the outer surface of the cage body and adapted for biting into the bone structure;

said threads defining means including a plurality of threads which define valleys therebetween, the threads defining turns with about 3 turns per cm to about 8 turns per cm;

a plurality of perforations provided in the valleys of the threads for providing communication between the outer surface and the cavity in order to allow immediate contact between the bone structures and the bone-growth-inducing substrate packed into the fusion cage; and wherein said perforations comprise at least from 30% to 60% of said inner surface.

142. The fusion cage of claim 141 wherein the cage body has a length of 20 mm to 25 mm.

143. A fusion cage adapted for promoting the fusion with bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity such that with the outer surface contacting the bone structures, there is immediate contact between the bone structures and the bone-growth-inducing substance packed into the internal cavity of the fusion cage;

said helical structure has valleys defined between said turns;

said means for providing immediate contact includes a multiplicity of perforations located in said valleys that provide communication between said outer surface and said internal cavity; and wherein said perforations comprise at least from 30% to 60% of said inner surface.

144. A fusion cage adapted for promoting the fusion with bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity such that with the outer surface contacting the bone structures, there is immediate contact between the bone structures and the bone-growth-inducing substance packed into the internal cavity of the fusion cage; and wherein said helical structure is fitted with removable perforated end caps.

145. A fusion cage adapted for promoting fusion with bone structures when bone-growth-inducing substance is packed into the fusion cage, comprising:

a cage body defining a cavity with an inner surface, said cavity adapted to be packed with bone-growth-inducing substance;

said cage body defining an outer surface comprised of a thread with a crown and with a plurality of turns and valleys defined between said turns;

a plurality of perforations defined in said valleys so that the inner surface contacts the outer surface in order to allow immediate contact between the bone structures and the bone-growth-inducing substance packed into the fusion cage; and wherein said perforations do not interrupt said crown of said thread.

146. A fusion cage adapted for promoting fusion with bone structures when bone-growth-inducing substance is packed into the fusion cage, comprising:

a cage body defining an internal cavity adapted to be packed with the bone-growth-inducing substance, which cage body defines an outer surface;

means defined on the outer surface of the cage body for mating the fusion cage to the bone structure, which means prevents the fusion cage from backing out from the bone structure;

means for providing immediate contact between the bone structures and the bone-growth-inducing substance packed into the fusion cage with the fusion cage mated to the bone structures so that the bone structures cross over the outer surface into the internal cavity and into contact with the bone-growth-inducing substance packed in the fusion cage.

147. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided only in the valleys of the threads for providing communication between the outer surface and the cavity in order to allow immediate contact between the bone structures and the bone-growth-inducing substance packed into the fusion cage.

148. A fusion cage adapted for promoting fusion with bone structures when bone-growth-inducing substance is packed into the fusion cage, comprising:

a cage body defining an cavity with an inner surface, said cavity adapted to be packed with bone-growth-inducing substance;

said cage body defining an outer surface comprised of a continuous thread with a plurality of turns and valleys defined between said turns;

a plurality of perforations defined in said valleys so that the inner surface contacts the outer surface in order to allow immediate contact between the bone structures and the bone-growth-inducing substance packed into the fusion cage.

149. A fusion cage adapted for promoting fusion with bone structures when bone-growth-inducing substance is packed into the fusion cage, comprising:

a cage body having an inner surface which defines a cavity adapted to be packed with the bone-growth-inducing substance;

said cage body defining an outer surface;

means defined on the outer surface of the cage body adapted for allowing the fusion cage to bite into the bone structure;

means for providing a plurality of sites where the inner surface contacts the outer surface in order to allow immediate contact between the bone structures and the bone-growth-inducing substance packed into the fusion cage; and wherein at least some of the sites are from about one millimeter in dimension both axially and transversely to about two millimeters axially and about three millimeters transversely in dimension to permit good ingrowth of bone and so as not to unduly weaken the cage.

150. A fusion cage adapted for promoting fusion with bone structures when bone-growth-inducing substance is packed into the fusion cage, comprising:

a helical structure having an inner surface which defines an internal cavity;

said helical structure having a substantially V-shaped outer surface pointing in a direction away from the internal cavity and adapted for biting into the bone structures;

said helical structure defining a plurality of spaced turns communicating with the internal cavity so that the inner surface intersects the outer surface forming elongated perforations along the direction of travel of said helical structure such that with the outer surface biting into the bone structures, there is immediate contact between the bone structures and the bone-growth-inducing substance packed into the internal cavity of the fusion cage.

151. A fusion cage adapted for promoting the fusion with bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity, and forming elongated perforations along the direction of said helical structure such that with the outer surface contacting the bone structures, there is immediate contact between the bone structures and the bone-growth-inducing substance packed into the internal cavity of the fusion cage.

152. A fusion cage adapted for promoting the fusion with bone structures when bone-growth-inducing substance is packed into the fusion cage, comprising:

a helical structure having an inner surface which defines an internal cavity;

said helical structure having a substantially V-shaped outer surface pointing in a direction away from the internal cavity and adapted for biting into the bone structure;

said helical structure defining a plurality of spaced turns communicating with the internal cavity so that the inner surface intersects the outer surface defining perforations such that with the outer surface biting into the bone structures, there is immediate contact between the bone structures and the bone-growth-inducing substance packed into the internal cavity of the fusion cage; and wherein at least some of the perforations are from about one millimeter in dimension about axially and transversely to about two millimeters axially and about three millimeters transversely in dimension to permit good ingrowth of bone and so as not to unduly weaken the cage.

153. A fusion cage adapted for promoting fusion with bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity to define perforations such that with the outer surface contacting the bone structures, there is immediate contact between the bone structures and the bone-growth-inducing substance packed into the internal cavity of the fusion cage;

said helical structure having valleys defined between said turns; and said inner surface pierces through the valleys to define a plurality of perforations whereby the inner surface contacts the outer surface and with the perforations having no substantial depth.

154. A fusion cage adapted for promoting fusion with bone structures when bone-growth-inducing substance is packed into the fusion cage, comprising:

a helical structure having an inner surface which defines an internal cavity;

said helical structure having an outer surface pointing in a direction away from the internal cavity and adapted for contacting bone structures;

said helical structure defining a plurality of spaced turns communicating with the internal cavity to define perforations such that with the outer surface contacting the bone structures, there is immediate contact between the bone structures and the bone-growth-inducing substance packed into the internal cavity of the fusion cage; and wherein at least some of the perforations are from about 1 millimeter in dimension both axially and transversely along the direction of said threads to about two millimeters in dimension axially and about three millimeters in dimension transversely along the direction of said threads to permit good ingrowth of bone and so as not to unduly weaken the cage.

155. A fusion cage adapted for promoting fusion with bone structures when bone-growth-inducing substance is packed into the fusion cage, comprising:

a cage body having an inner surface which defines a cavity adapted to be packed with the bone-growth-inducing substance;

said cage body defining an outer surface;

means defined on the outer surface of the cage body adapted for allowing the fusion cage to bite into the bone structure;

means for providing a plurality of sites where the cavity contacts the outer surface in order to allow immediate contact between the bone structures and the bone-growth-inducing substance packed into the fusion cage.

156. A fusion cage adapted for promoting fusion of bone structures when bone-growth-inducing substance is packed into the fusion cage, comprising:

a cage body defining a cavity with an inner surface, said cavity adapted to be packed with the bone-growth-inducing substance;

said cage body defining an outer surface;

means for defining threads on the outer surface of the cage body and adapted for biting into the bone structure;

said threads defining means including a plurality of threads which define valleys therebetween;

a plurality of perforations provided in the valleys of the threads for providing communication between the outer surface and the cavity in order to allow immediate contact between the bone structures and the bone-growth-inducing substance packed into the fusion cage; and wherein said perforations comprise about 50% of said inner surface.

157. A surgical method for fusing a fusion cage between two vertebrae comprising the steps of:

forming a bore in the vertebrae;

screwing the fusion cage into the bore, which fusion cage includes:

a. a cage body defining an internal cavity, which cage body defines an outer surface;

b. means defined on the outer surface of the cage body for mating the fusion cage to the vertebrae, which means prevents the fusion cage from backing out from the vertebrae; and c. means for providing immediate contact between the vertebrae and a bone-growth-inducing substance packed into the fusion cage when the fusion cage is mated to the vertebrae so that the vertebrae cross over the outer surface into the internal cavity and into contact with bone-growth-inducing substance packed in the fusion cage;

said screwing step further causes the vertebrae to cross over the outer surface into the internal cavity of the fusion cage; and packing the fusion cage with bone-growth-inducing substance.

158. A surgical method for fusing a fusion cage between two vertebrae comprising the steps of:

forming a bore in the vertebrae;

screwing the fusion cage into the bore, which fusion cage includes:

a. a cage body having an inner surface which defines a cavity;

b. said cage body defining an outer surface;

c. means defined on the outer surface of the cage body for allowing the fusion cage to bite into the vertebrae, and d. means for providing a plurality of sites where the inner surface contacts the outer surface in order to allow immediate contact between the vertebrae and a bone-growth-inducing substance packed into the fusion cage; and packing the fusion cage with bone-growth-inducing substance.

159. A surgical method for fusing a fusion cage between two vertebrae comprising the steps of:

forming a bore in the vertebrae;

screwing the fusion cage into the bore, which fusion cage includes:

a. a cage body defining a cavity with an inner surface;

b. said cage body defining an outer surface;

c. means for defining threads on the outer surface of the cage body for biting into the vertebrae;

d. said threads defining means including a plurality of threads which define valleys therebetween; and e. a plurality of perforations provided in the valleys of the threads for providing communication between the outer surface and the cavity in order to allow immediate contact between the vertebrae and a bone-growth-inducing substance packed into the fusion cage; and packing the fusion cage with bone-growth-inducing substance.

160. A surgical method for fusing a fusion cage between two vertebrae comprising the steps of:

forming a bore in the vertebrae;

screwing the fusion cage into the bore, which fusion cage includes:

a. a cage body defining a cavity with an inner surface;

b. said cage body defining an outer surface comprised of a substantially continuous thread with a plurality of turns and valleys defined between said turns; and c. a plurality of perforations defined in said valleys so that the inner surface contacts the outer surface in order to allow immediate contact between the vertebrae and a bone-growth-inducing substance packed into the fusion cage; and packing the fusion cage with bone-growth-inducing substance.

161. A surgical method for fusing a fusion cage between two vertebrae comprising the steps of:

forming a bore in the vertebrae;

screwing the fusion cage into the bore, which fusion cage includes:
  a. a cage body defining a cavity with an inner surface;
  b. said cage body defining an outer surface comprised of a substantially continuous thread with a plurality of turns and valleys defined between said turns; and
  c. said cavity defining a plurality of channels which pierce through the valleys to define a plurality of perforations whereby the inner surface contacts the outer surface so that there is immediate contact between the vertebrae and a bone-growth-inducing subtance packed into the fusion cage; and packing the fusion cage with bone-growth-inducing substance.

162. A surgical method for fusing a fusion cage between two vertebrae comprising the steps of:

forming a bore in the vertebrae;
screwing the fusion cage into the bore, which fusion cage includes:
  a. a plurality of spaced elongate members which define an internal cavity;
  b. said elongate members having an inner surface that faces the internal cavity and an outer surface that faces away from the internal cavity;
  c. a helical thread member formed about and connected to the outer surfaces of the spaced elongate members, which helical thread member defines a plurality of turns; and
  d. a plurality of apertures defined between turns, which apertures are bordered by the spaced elongate members, wherein the thread member contacts between the vertebrae and a bone-growth-inducing substance packed into the fusion cage; and packing the fusion cage with bone-growth-inducing substance.

163. A surgical method for fusing a fusion cage between two vertebrae comprising the steps of:

forming a bore in the vertebrae;
screwing the fusion cage into the bore, which fusion cage includes:
  a. a helical structure having an inner surface which defines an internal cavity;
  b. said helical structure having an outer surface pointing in a direction away from the internal cavity and for contacting the vertebrae; and
  c. said helical structure defining a plurality of spaced turns communicating with the internal cavity such that with the outer surface contacting the vertebrae, there is immediate contact between the vertebrae and a bone-growth-inducing substance packed into the internal cavity of the fusion cage; and packing the fusion cage with bone-growth-inducing substance.

164. A surgical method for fusing a fusion cage between two vertebrae comprising the steps of:

forming a bone in the vertebrae;
screwing the fusion cage into the bone, which fusion cage includes:
  a. a helical structure having an inner surface which defines an internal cavity;
  b. said helical structure having an outer surface pointing in a direction away from the internal cavity and for contacting the vertebrae; and
  c. said helical structure defining a plurality of spaced turns communicating with the internal cavity such that with the outer surface contacting the vertebrae, there is immediate contact between the vertebrae and bone-growth-inducing substance packed into the internal cavity of the fusion cage; and packing the fusion cage with bone-growth-inducing substance.

* * * * *